(12) United States Patent
Sugahara

(10) Patent No.: US 7,946,183 B2
(45) Date of Patent: May 24, 2011

(54) BENDING-DETECTION APPARATUS

(75) Inventor: Hiroto Sugahara, Aichi-ken (JP)

(73) Assignee: Brother Kogyo Kabushiki Kaisha, Aichi-Ken (JP)

( * ) Notice: Subject to any disclaimer, the term of this patent is extended or adjusted under 35 U.S.C. 154(b) by 21 days.

(21) Appl. No.: 12/286,401

(22) Filed: Sep. 30, 2008

(65) Prior Publication Data

US 2009/0084190 A1 Apr. 2, 2009

(30) Foreign Application Priority Data

Oct. 1, 2007 (JP) ................................ 2007-257249

(51) Int. Cl.
*G01N 3/20* (2006.01)
(52) U.S. Cl. ........................................ 73/849; 73/760
(58) Field of Classification Search ............. 73/760–849
See application file for complete search history.

(56) References Cited

U.S. PATENT DOCUMENTS

| 5,260,926 | A | * | 11/1993 | Kuroda et al. | 369/100 |
| 5,365,799 | A | * | 11/1994 | Okada | 73/862.041 |
| 5,445,185 | A | * | 8/1995 | Watanabe et al. | 137/596.17 |
| 7,127,948 | B2 | * | 10/2006 | Tavares et al. | 73/514.34 |
| 2008/0036333 | A1 | * | 2/2008 | Funakubo et al. | 310/323.02 |
| 2009/0085866 | A1 | * | 4/2009 | Sugahara | 345/156 |
| 2010/0247133 | A1 | * | 9/2010 | Sugahara | 399/81 |

FOREIGN PATENT DOCUMENTS

| JP | 10-022509 | 1/1998 |
| JP | 10-054842 | 2/1998 |
| JP | 2006-292440 | 10/2006 |

* cited by examiner

*Primary Examiner* — Max Noori
(74) *Attorney, Agent, or Firm* — Frommer Lawrence & Haug LLP

(57) ABSTRACT

A bending-detection apparatus includes a sheet-shaped substrate having flexibility and a bending-detection mechanism including a sensor which measures a potential difference to detect bending deformations of the substrate and two bending-detection sections which are arranged on a surface of the substrate at different areas respectively. Each of the bending-detection sections has a piezoelectric layer provided on a surface of the substrate; plurality of first electrodes which are conducted with each other and each of which extends on a surface of the piezoelectric layer along a direction; a plurality of second electrodes which are arranged alternately with the plurality of first electrodes. An electrode-extending direction in which the first and second electrodes extend is different between the two bending-detection sections. Consequently, a bending-detection apparatus capable of detecting bending deformations in the substrate in various directions is provided.

10 Claims, 21 Drawing Sheets

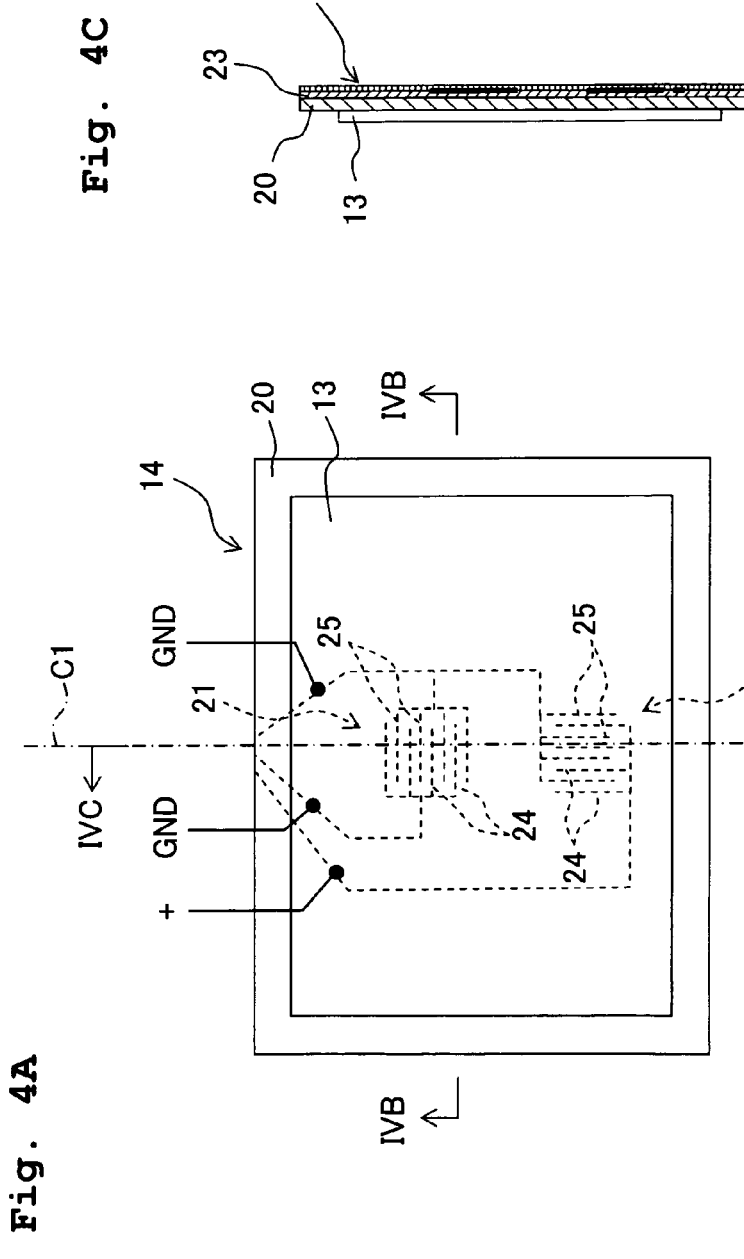
Fig. 4A
Fig. 4C
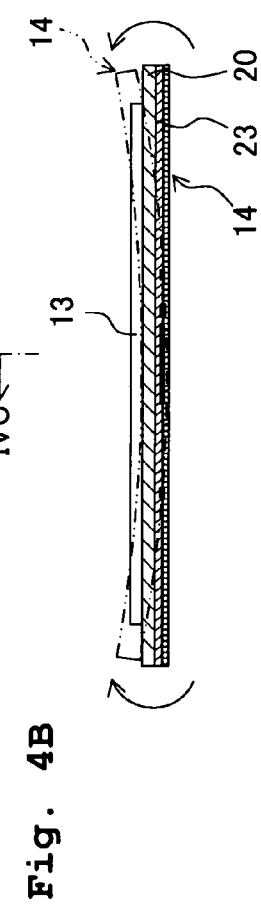
Fig. 4B

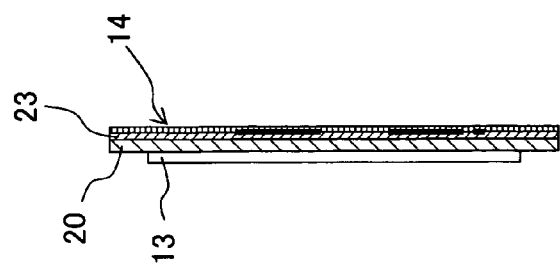
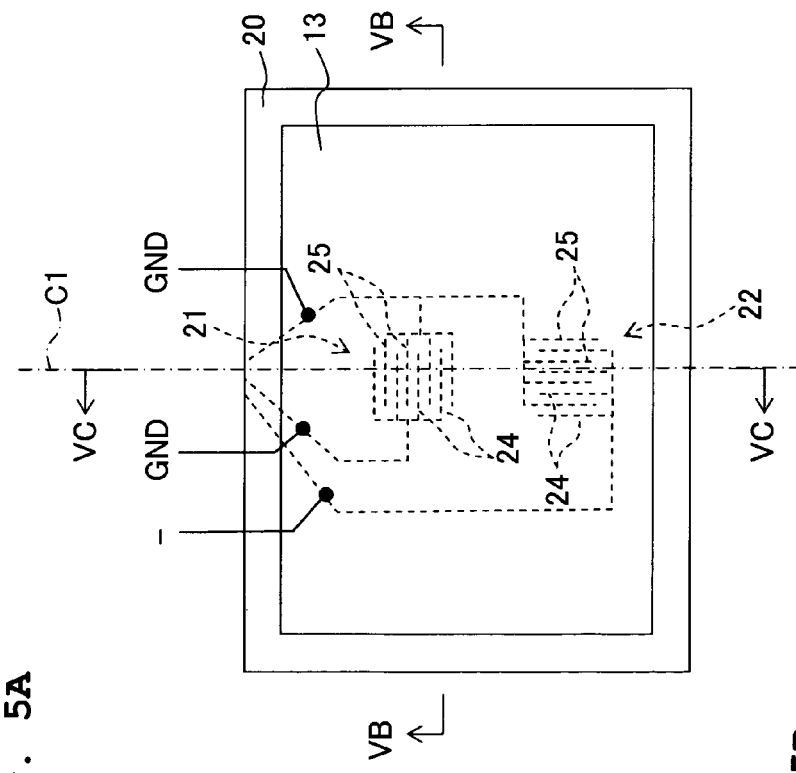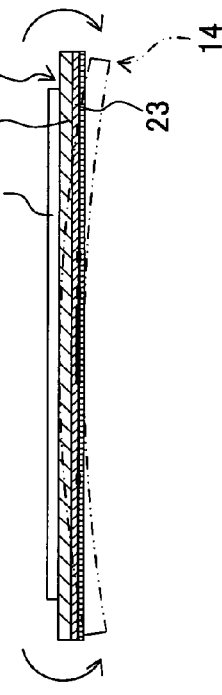

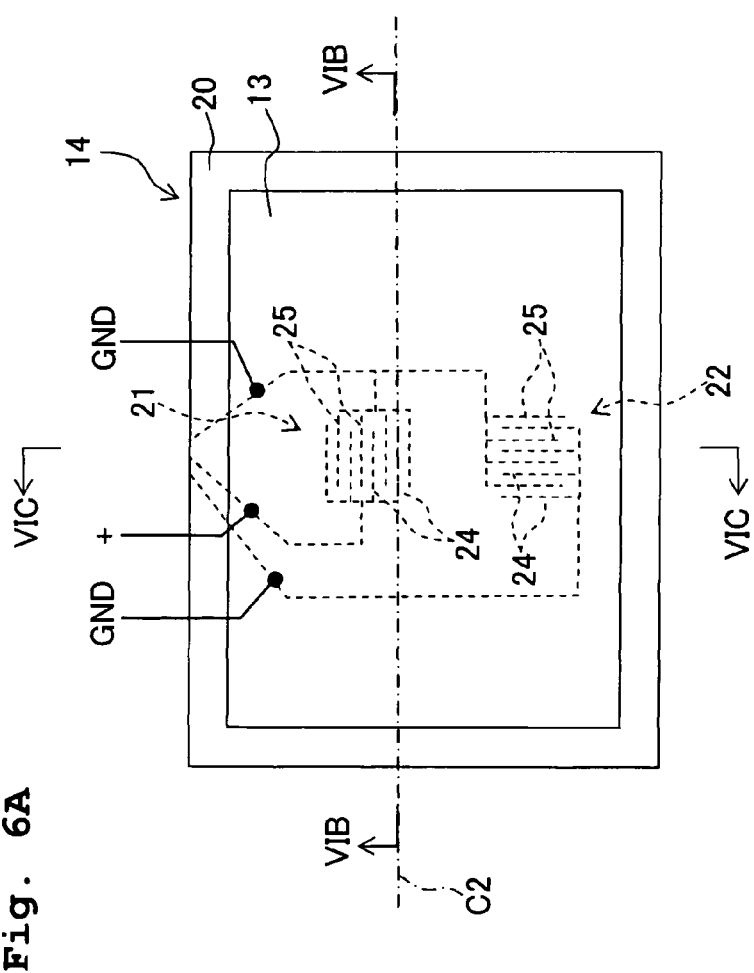
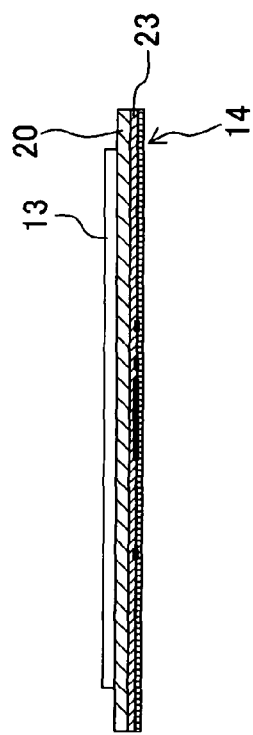

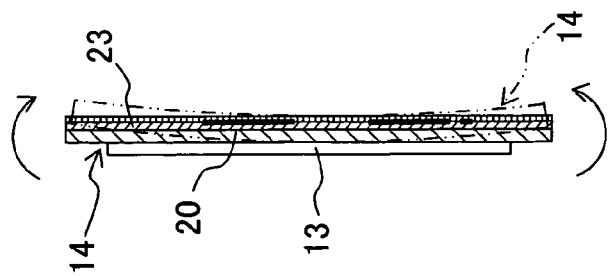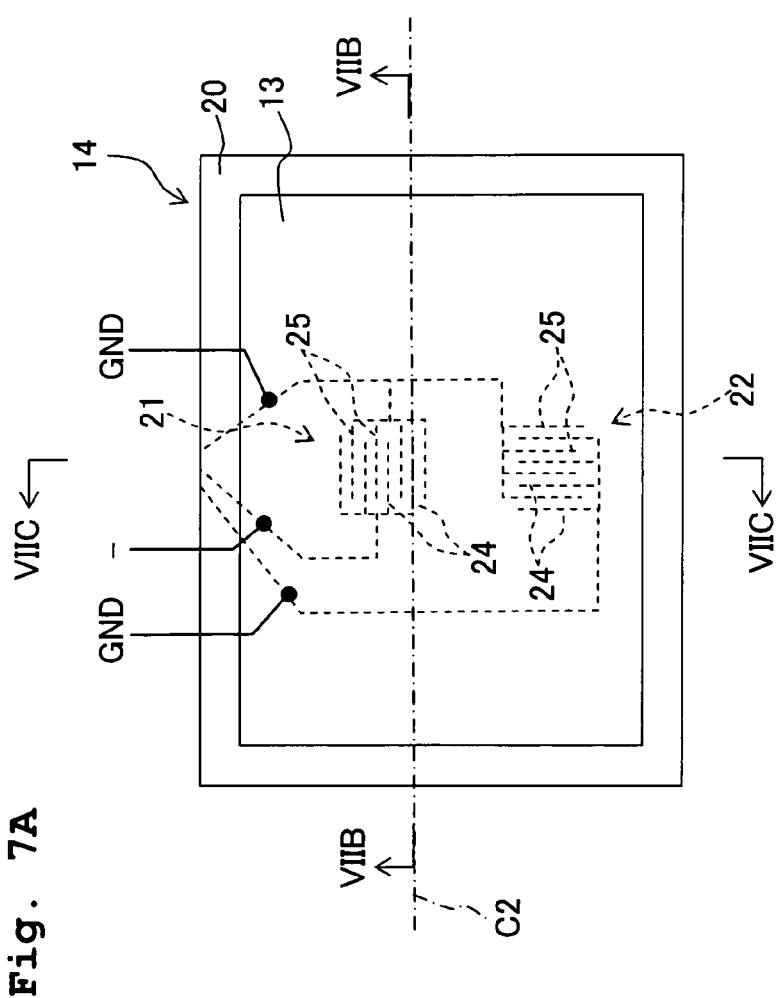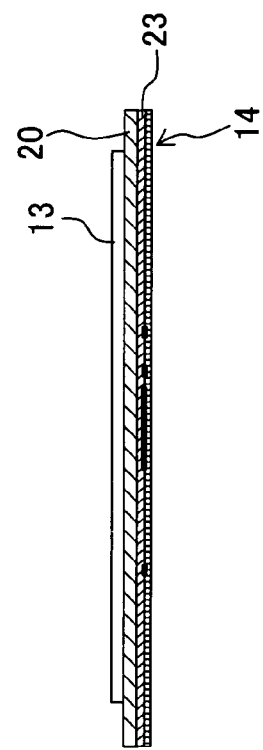

Fig. 8A

| ITEM | OPERATION OF USER | | FIRST ELECTRODE ELECTRIC POTENTIAL | |
|---|---|---|---|---|
| | BENDING AXIS | DIRECTION OF PROJECTION OF SUBSTRATE | FIRST BENDING DETECTION SECTION | SECOND BENDING DETECTION SECTION |
| A | C1 | DOWNWARD | GND | + |
| B | C1 | UPWARD | GND | − |
| C | C2 | DOWNWARD (BENDING SPEED – LOW) | + (LOW) | GND |
| D | C2 | UPWARD (BENDING SPEED – LOW) | − (LOW) | GND |
| E | C2 | DOWNWARD (BENDING SPEED – HIGH) | + (HIGH) | GND |
| F | C2 | UPWARD (BENDING SPEED – HIGH) | − (HIGH) | GND |

(NOTE) 'BENDING AXIS C1' IS AN AXIS PARALLEL TO SHORT-SIDE DIRECTION (DIRECTION OF SHORT SIDE) OF SUBSTRATE.
'BENDING AXIS C2' IS AN AXIS PARALLEL TO LONGITUDINAL DIRECTION (DIRECTION OF LONG SIDE) OF SUBSTRATE.

Fig. 8B

| ITEM | PROCESS CONTENT |
|---|---|
| A | REDUCTION (CONTRACTION) OF IMAGE |
| B | ENLARGEMENT OF IMAGE |
| C | SWITCH TO IMAGE OF SUBSEQUENT DATA |
| D | SWITCH TO IMAGE OF PREVIOUS DATA |
| E | SWITCH TO IMAGE OF DATA AFTER FIVE DATA |
| F | SWITCH TO IMAGE OF DATA BEFORE FIVE DATA |

Fig. 11A

| ITEM | OPERATION OF USER | | |
|---|---|---|---|
| | BENDING AXIS | BENDING POSITION | DIRECTION OF PROJECTION OF SUBSTRATE |
| A | C1 | CENTRAL PORTION | DOWNWARD |
| B | C1 | CENTRAL PORTION | UPWARD |
| C | C1 | RIGHT END PORTION | DOWNWARD |
| D | C1 | RIGHT END PORTION | UPWARD |
| E | C1 | LEFT END PORTION | DOWNWARD |
| F | C1 | LEFT END PORTION | UPWARD |
| G | C2 | UPPER END PORTION | DOWNWARD |
| H | C2 | UPPER END PORTION | UPWARD |
| I | C2 | LOWER END PORTION | DOWNWARD |
| J | C2 | LOWER END PORTION | UPWARD |

(NOTE) 'BENDING AXIS C1' IS AN AXIS PARALLEL TO SHORT-SIDE DIRECTION (DIRECTION OF SHORT SIDE) OF SUBSTRATE

Fig. 11B

| ITEM | FIRST ELECTRODE ELECTRIC POTENTIAL | | | | | PROCESS CONTENT |
|---|---|---|---|---|---|---|
| | DETECTING SECTION (UPPER) | DETECTING SECTION (LOWER) | DETECTING SECTION (CENTRAL) | DETECTING SECTION (LEFT) | DETECTING SECTION (RIGHT) | |
| A | GND | GND | + | GND | GND | CONTRACT AT CENTRAL PORTION |
| B | GND | GND | − | GND | GND | EXPAND AT CENTRAL PORTION |
| C | GND | GND | GND | GND | + | CONTRACT AT RIGHT END PORTION |
| D | GND | GND | GND | GND | − | EXPAND AT RIGHT END PORTION |
| E | GND | GND | GND | + | GND | CONTRACT AT LEFT END PORTION |
| F | GND | GND | GND | − | GND | EXPAND AT LEFT END PORTION |
| G | + | GND | GND | GND | GND | CONTRACT AT UPPER END PORTION |
| H | − | GND | GND | GND | GND | EXPAND AT UPPER END PORTION |
| I | GND | + | GND | GND | GND | CONTRACT LOWER END PORTION |
| J | GND | − | GND | GND | GND | EXPAND AT LOWER END PORTION |

Fig. 13A

| ITEM | BENDING AXIS | OPERATION OF USER |
|---|---|---|
| | | DIRECTION OF PROJECTION OF SUBSTRATE |
| A | C1 | DOWNWARD |
| B | C1 | UPWARD |
| C | C2 | DOWNWARD (BENDING SPEED – LOW) |
| D | C2 | UPWARD (BENDING SPEED – LOW) |
| E | C2 | DOWNWARD (BENDING SPEED – HIGH) |
| F | C2 | UPWARD (BENDING SPEED – HIGH) |
| G | C3 | DOWNWARD |
| H | C3 | UPWARD |

(NOTE) 'BENDING AXIS C1' IS AN AXIS PARALLEL TO SHORT-SIDE DIRECTION (DIRECTION OF SHORT SIDE) OF SUBSTRATE.
'BENDING AXIS C2' IS AN AXIS PARALLEL TO LONGITUDINAL DIRECTION (DIRECTION OF LONG SIDE) OF SUBSTRATE.
'BENDING AXIS C3' IS AN AXIS INCLINED AT 45° TOWARD LEFT WITH RESPECT TO SHORT-SIDE DIRECTION OF SUBSTRATE.

Fig. 13B

| ITEM | FIRST ELECTRODE ELECTRIC POTENTIAL ||| PROCESS CONTENT |
|---|---|---|---|---|
| | FIRST BENDING DETECTION SECTION | SECOND BENDING DETECTION SECTION | THIRD BENDING DETECTION SECTION | |
| A | GND | + | GND | REDUCTION OF IMAGE |
| B | GND | − | GND | ENLARGEMENT OF IMAGE |
| C | + (LOW) | GND | GND | SWITCH TO IMAGE OF SUBSEQUENT DATA |
| D | − (LOW) | GND | GND | SWITCH TO IMAGE OF PREVIOUS DATA |
| E | + (HIGH) | GND | GND | SWITCH OF IMAGE OF DATA AFTER FIVE DATA |
| F | − (HIGH) | GND | GND | SWITCH TO IMAGE OF DATA BEFORE FIVE DATA |
| G | GND | GND | + | IMAGE PROCESSING STARTS |
| H | GND | GND | − | IMAGE PROCESSING DISCONTINUED |

Fig. 17A

| ITEM | OPERATION OF USER | | |
|---|---|---|---|
| | BENDING AXIS | BENDING POSITION | DIRECTION OF PROJECTION OF SUBSTRATE |
| A | C1 | CENTRAL | DOWNWARD |
| B | C1 | CENTRAL | UPWARD |
| C | C1 | RIGHT END | DOWNWARD |
| D | C1 | RIGHT END | DOWNWARD |
| E | C2 | UPPER END | DOWNWARD |
| F | C2 | LOWER END | DOWNWARD |

(NOTE) 'BENDING AXIS C1' IS AN AXIS PARALLEL TO SHORT-SIDE DIRECTION (DIRECTION OF SHORT SIDE) OF SUBSTRATE.
'BENDING AXIS C2' IS AN AXIS PARALLEL TO LONGITUDINAL DIRECTION (DIRECTION OF LONG SIDE) OF SUBSTRATE.

Fig. 17B

| ITEM | FIRST ELECTRODE ELECTRIC POTENTIAL ||||| PROCESS CONTENT |
|---|---|---|---|---|---|---|
| | DETECTING SECTION (UPPER) | DETECTING SECTION (LOWER) | DETECTING SECTION (CENTRAL) | DETECTING SECTION (LEFT) | DETECTING SECTION (RIGHT) | |
| A | GND | GND | + | GND | GND | INCREASE IN NUMBER OF DISPLAY IMAGES (THUMBNAIL DISPLAY) |
| B | GND | GND | − | GND | GND | DECREASE IN NUMBER OF DISPLAY IMAGES (STANDARD DISPLAY) |
| C | GND | GND | GND | GND | + | SELECT IMAGE AT RIGHT |
| D | GND | GND | GND | + | GND | SELECT IMAGE AT LEFT |
| E | + | GND | GND | GND | GND | SELECT UPPER IMAGE |
| F | GND | + | GND | GND | GND | SELECT LOWER IMAGE |

BENDING-DETECTION APPARATUS

CROSS REFERENCE TO RELATED APPLICATION

The present application claims priority from Japanese Patent Application No. 2007-257249, filed on Oct. 1, 2007, the disclosure of which is incorporated herein by reference in its entirety.

BACKGROUND OF THE INVENTION

1. Field of the Invention

The present invention relates to a bending-detection apparatus detecting a bending deformation when a sheet-shaped substrate is bent.

2. Description of the Related Art

Conventionally, a bending-detection apparatus in which a bending deformation of a substrate occurred in an external force acted is detected by a piezoelectric transducer being one kind of machinery (distortion) electrical conversion elements has been known. For example, the detecting apparatus (an external force detection sensor) written in Japanese Patent Application Laid-open No. H10-54842 is provided on a piezoelectric board in a cantilever shape, and has a piezoelectric supporting beam (the substrate) in which a plurality of grooves parallel each other are formed in the surface of the piezoelectric board and a plurality of electrodes formed respectively in the plurality of grooves of the piezoelectric supporting beam. The lead-out directions of two adjacent electrodes of the plurality of electrodes are mutually opposite direction, and the electrodes whose lead-out directions are same conduct each other. Namely, it is configured such that two kinds of comb tooth shaped electrodes consisting of the electrodes conducting each other exist on the surface of the piezoelectric supporting beam, and these two kinds of tooth shaped electrodes are disposed alternately thereon.

Suppose that stretch or compression is occurred in a direction perpendicular to the electrodes extending direction in a portion sandwiched between the two kinds of electrodes on the surface of the piezoelectric supporting beam when a bending deformation is occurred in the piezoelectric supporting beam by an external force in the detecting apparatus in Japanese Patent Application Laid-open No. H10-54842. When the piezoelectric supporting beam is polarized in a direction perpendicular to the extending direction of the electrodes, the deformation direction of the piezoelectric supporting beam (a stretch direction) becomes parallel to the polarization direction. Therefore, an electric field in a direction perpendicular to the extending direction of the electrodes is obtained between the two kinds of electrodes, and then a voltage (a potential difference) is generated between the electrodes. This makes it possible to detect a bending deformation occurred in the piezoelectric supporting beam.

SUMMARY OF THE INVENTION

However, the two kinds of comb tooth shaped electrodes disposed alternately can only detect a bending deformation in the piezoelectric supporting beam of the case of being stretched or compressed in a direction perpendicular to the extending direction of these two kinds of electrodes. Namely, when the piezoelectric supporting beam is stretched or compressed in a direction parallel to the extending direction of the electrodes, an electric field is not obtained between the two kinds of electrodes, and a voltage is not generated between both electrodes. This makes it impossible to detect a deformation in the piezoelectric supporting beam like this.

An object of the present invention is to provide a bending-detection apparatus capable of respectively detecting bending deformations of the substrate, of which bending directions are different from each other.

According to an aspect of the present invention, which detects a bending of a device, comprising:

a sheet-shaped substrate having flexibility;

a detecting mechanism which detects a bending deformation of the substrate and which includes a sensor measuring an electric potential difference, and a plurality of detecting sections arranged on a surface of the substrate at a plurality of areas, respectively, each of the detecting sections having: a piezoelectric layer provided on a surface of the substrate; a plurality of first electrodes which are conducted with each other and each of which extends in an extending direction on a surface of the piezoelectric layer; and a plurality of second electrodes which are conducted with each other and each of which extends on the surface of the substrate in the extending direction, and which are arranged on the surface of the substrate alternately with the plurality of first electrodes, wherein the sensor measures an electric potential difference between a first electrode and a second electrode, among the plurality of first and second electrodes, of each of the detecting sections, to detect the bending deformation of the substrate based on the measured potential difference, and the extending direction in which the first and second electrodes extend is different among the plurality of detecting sections.

According to the first aspect of the present invention, each of the detecting sections in the detecting mechanism has the plurality of first electrodes and the plurality of second electrodes disposed alternately on one surface of the piezoelectric layer. Therefore, when a distortion of compression or stretch is occurred in a direction perpendicular to the electrodes extending direction on the one surface of the piezoelectric layer by the substrate bent by an external force, a potential difference between the first electrode and the second electrode is obtained depending on the distortion. This leads a bending deformation in the substrate to be detected. Further, the plurality of detecting sections are provided on the substrate, and the extending directions of the electrodes (the first electrodes and the second electrodes) are different among these plurality of detecting sections. Consequently, it is possible to detect plural kinds of bending deformations occurred in the substrate, of which bending directions are different from each other, in the plurality of detecting sections.

In the bending-detection apparatus of the present invention, a thickness of the substrate may be locally thinned in areas, of the substrate, at which at least one of the detecting sections is arranged respectively.

In this manner, when the substrate is locally thin in the area where at least one of the detecting sections is disposed, the substrate gets deformed easily, and then a potential difference generated between the first electrode and the second electrode of when the substrate is deformed becomes large. Consequently, this makes the detecting sections easier to detect a bending deformation in the substrate.

In the bending-detection apparatus of the present invention, the first electrodes and the second electrodes may be arranged on a surface, of the piezoelectric layer, not facing the substrate; and an insulating layer which covers the first electrodes and the second electrodes on the surface, may be provided on the surface of the piezoelectric layer.

The insulating layer is provided to cover the electrodes on the piezoelectric layer in the case when the electrodes are disposed on the opposite surface to the substrate of the piezoelectric layer. Accordingly, in this case, a short cut and a failure of the electrodes and the like caused by the electrodes being exposed to the surface of the piezoelectric layer can be prevented.

The bending-detection apparatus of the present invention may further include a display which has flexibility, which is provided integrally with the substrate, and which displays an image; and a display control mechanism which controls the display to change an image displayed on the display, based on the bending deformation of the substrate detected in the detecting mechanism.

In this case, when a bending deformation is occurred in the sheet-shaped substrate having flexibility as if to fold paper, a bending deformation in the substrate is detected in a bending-detection mechanism, and further based on the detected bending deformation, an image to be displayed on the display is changed in the display control mechanism. Accordingly, an image to be displayed on the display can be changed easily by bending the substrate while looking at an image being displayed on the display.

In the bending-detection apparatus of the present invention, the piezoelectric layer may be arranged on a surface, of the substrate, not facing the display of the substrate.

The piezoelectric layer and the display section are disposed on the opposite sides sandwiching the substrate. In this structure, compared with the case when three layers are stacked in the order of the substrate, the piezoelectric layer, and the display section (namely, the case when the piezoelectric layer exists between the substrate and the display section), a distance from a neutral line of a curvature of the three-layered structure to the piezoelectric layer becomes large. This contributes to a large distortion formed in the piezoelectric layer when the substrate is bent, it makes it easier to detect a bending deformation in the substrate in the detecting mechanism.

In the bending-detection apparatus of the present invention, the substrate may have a rectangular shape; and the detecting mechanism may includes two detecting sections arranged in a center line of a side among sides defining the substrate, and the first and the second electrodes in one of the two detecting sections may extend parallel to the one side, and the first and the second electrodes in the other of the two detecting sections may extend in a direction perpendicular to the one side.

In this structure, the detecting mechanism includes the detecting section having the first, and the second electrodes extending parallel to a single side of the substrate, and the detecting section having the first, and the second electrodes extending in a direction perpendicular to a single side of the substrate. Consequently, even in the case when the substrate is bent in either direction, the direction parallel to a single side or the direction perpendicular to a single side, the detecting mechanism can detect a curvature of the substrate.

In the bending-detection apparatus of the present invention, the substrate may have a rectangular shape; and the detecting mechanism may further include another detecting section arranged at a corner of the substrate, and an angle defined by one side of the corner and the extending direction in which the first and the second electrodes extend in each of the detecting sections, and another angle defined by the other side of the corner and the extending direction are both approximately 45 degrees. In this structure, the detecting section having the electrodes inclined diagonally toward the sides of the substrate is disposed at the corner of the substrate, which makes it possible to detect the operation of bending the corner of the substrate easily.

In the bending-detection apparatus of the present invention, the substrate may have a rectangular shape; and the detecting mechanism may include four detecting sections each of which is arranged adjacent to a center of one of four sides defining the substrate, and an extending direction in which the first and the second electrodes extend in each of the detecting sections arranged adjacent to one of the four sides may be approximately parallel to one of the four sides. In this structure, the detecting sections are disposed respectively at the center of the four sides of the substrate having a rectangular shape, which makes it possible to detect curvatures of the substrate of when the substrate having a rectangular shape is bent in a longitudinal direction and a lateral direction efficiently.

In the bending-detection apparatus of the present invention, the second electrodes in each of the detecting sections may be conducted with each other and may be grounded. In this structure, all the second electrodes conduct. Therefore, it can be grounded at one point in order to ground the second electrodes, which makes it possible to simplify wiring.

In the bending-detection apparatus of the present invention, an area, of the piezoelectric layer, sandwiched between the first and the second electrodes in each of the detecting sections may be polarized parallel to a direction from the second electrodes toward the first electrodes. In this structure, since the piezoelectric layer is polarized in a predetermined direction beforehand, it is not necessary to perform a polarization process for the piezoelectric layer before using the bending-detection apparatus.

According to the present invention, plural detecting sections are provided on the substrate, and the extending directions of the electrodes (the first electrodes and the second electrodes disposed alternately) are different among these plural detecting sections. Consequently, plural kinds of bending deformations formed in the substrate, whose curvature directions are different, can be detected respectively in the plural detecting sections.

BRIEF DESCRIPTION OF THE DRAWINGS

FIG. 3A is a plan view, and FIG. 3B is a sectional view taken along the IIIB-IIIB line of FIG. 3A;

FIGS. 4A, 4B, and 4C are views showing a state of the input device of when the substrate is bent toward the reverse side of the sheet to be convex around an axis C1, FIG. 4A is a plan view, FIG. 4B is a sectional view taken along the IVB-IVB line of FIG. 4A, and FIG. 4C is a sectional view taken along the VIC-VIC line of FIG. 4A;

FIGS. 5A, 5B, and 5C are views showing a state of the input device of when the substrate is bent toward the front side of the sheet to be convex around the axis C1, FIG. 5A is a plan view, FIG. 5B is a sectional view taken along the VB-VB line of FIG. 5A, and FIG. 5C is a sectional view taken along the VC-VC line of FIG. 5A;

FIGS. 6A, 6B, and 6C are views showing a state of the input device of when the substrate is bent toward the reverse side of the sheet to be convex around an axis C2, FIG. 6A is a plan view, FIG. 6B is a sectional view taken along the VIB-VIB line of FIG. 6A, and FIG. 6C is a sectional view taken along the VIC-VIC line of FIG. 6A;

FIGS. 7A, 7B, and 7C are views showing a state of the input device of when the substrate is bent toward the front side of the sheet to be convex around the axis C2, FIG. 7A is a plan view, FIG. 7B is a sectional view taken along the VIIB-VIIB line of FIG. 7A, and FIG. 7C is a sectional view taken along the VIIC-VIIC line of FIG. 7A;

FIGS. 8A and 8B are tables showing the contents of an image change process assigned to aspects of bending deformations in the substrate;

FIGS. 11A and 11B are tables showing the contents of the image change process assigned to aspects of bending deformations in the substrate of the second modified form;

FIGS. 13A and 13B are tables showing the processing contents assigned to aspects of bending deformations of the third modified form;

FIG. 14A is a plan view, and FIG. 14B is a sectional view taken along the XIVB-XIVB line of FIG. 14A;

FIG. 15A is a plan view, and FIG. 15B is a sectional view taken along the XVB-XVB line of FIG. 15A;

FIGS. 17A and 17B are tables showing the contents of the image change process assigned to aspects of bending deformations in the substrate of the sixth modified form.

DETAILED DESCRIPTION OF THE PREFERRED EMBODIMENTS

Figure 1:
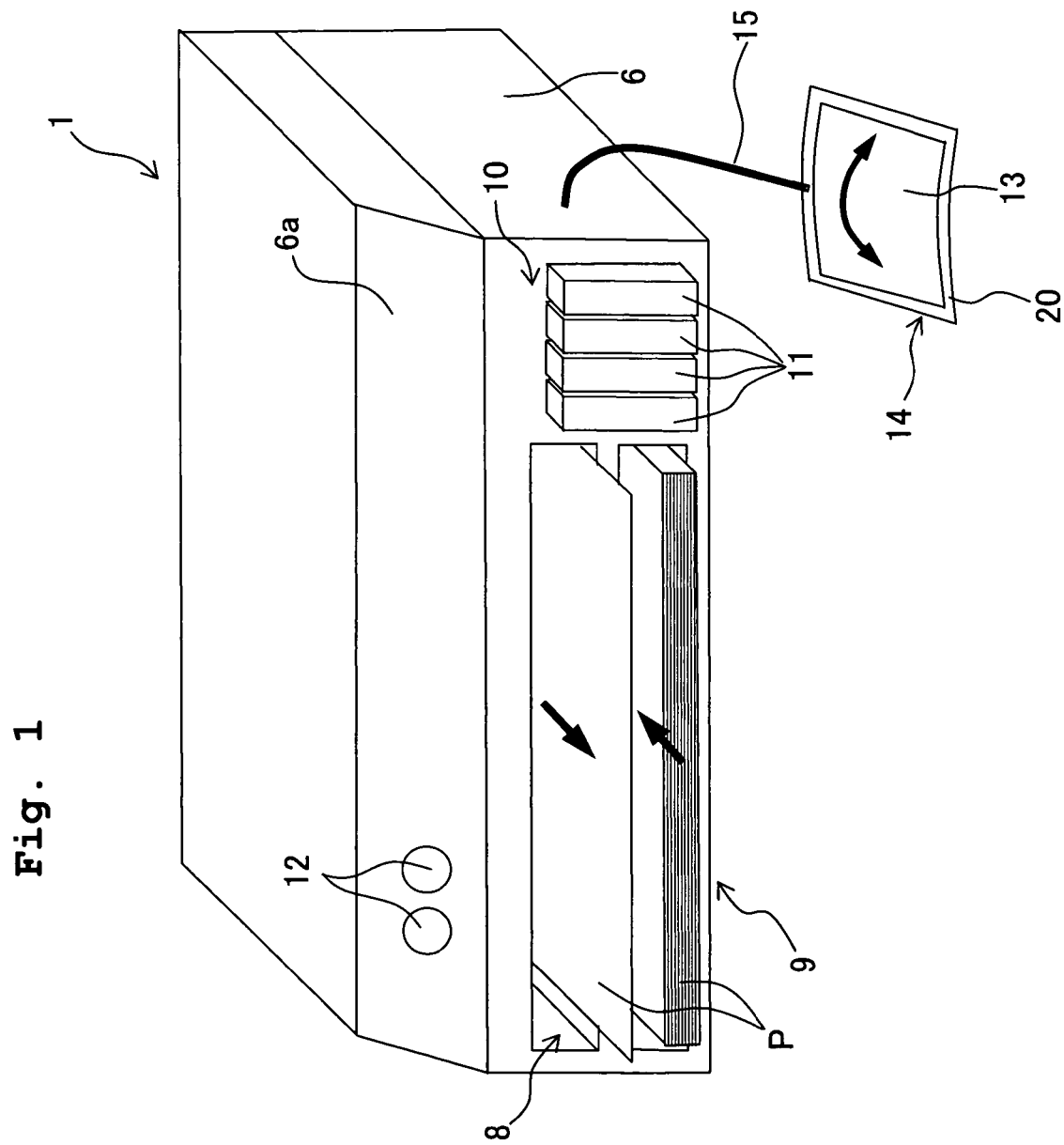
FIG. 1 is a schematic perspective view of a printer according to an embodiment of the present invention.

Next, embodiments of the present invention will be explained. FIG. 1 is a perspective view of a printer in this embodiment, and FIG. 2 is a block diagram schematically showing the electrical configuration of the printer.

Figure 2:
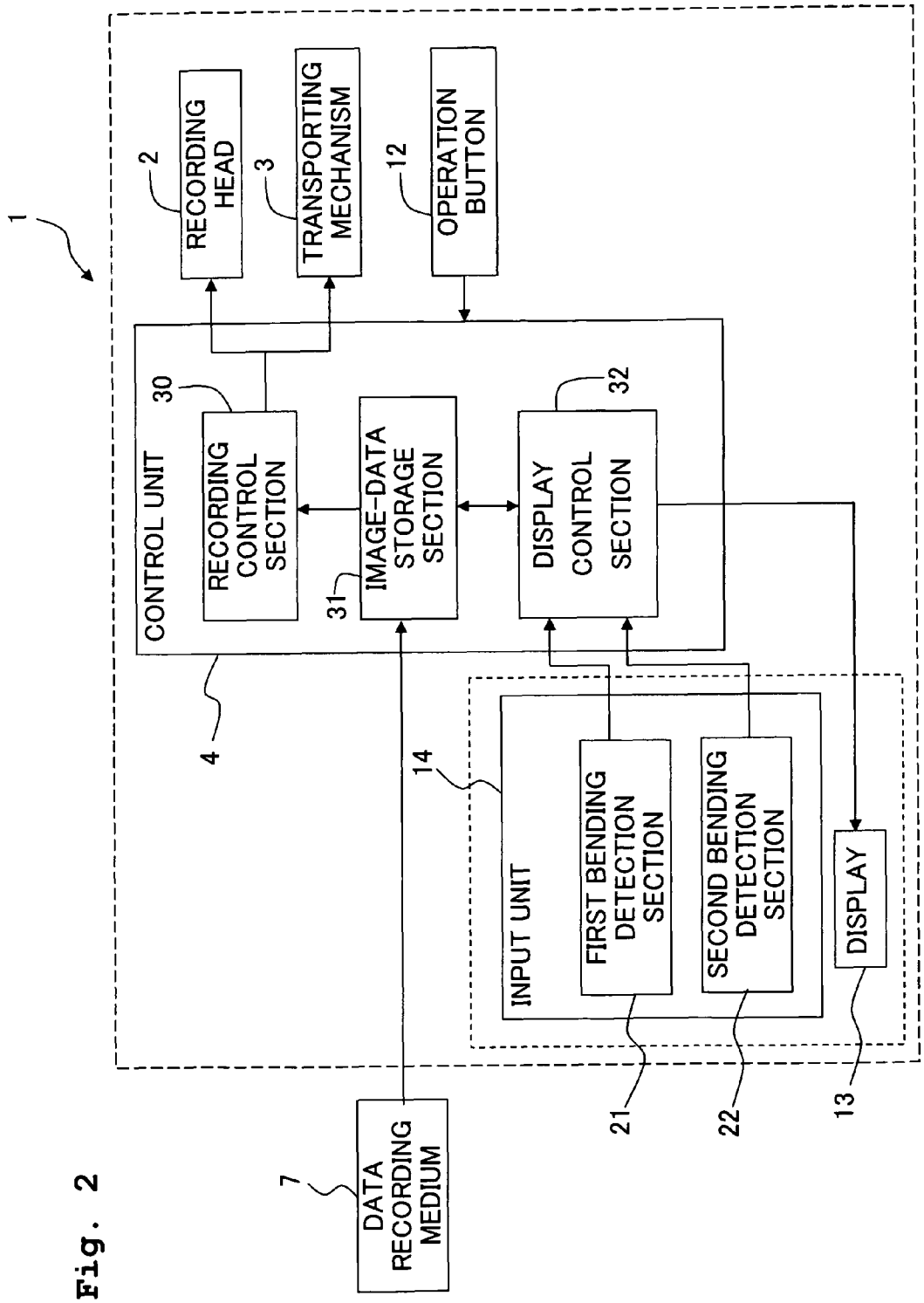
FIG. 2 is a block diagram schematically showing the electrical configuration of the printer of this embodiment.

As shown in FIGS. 1 and 2, a printer 1 of this embodiment includes: a recording head 2 recording an image on a printing paper P; a transport mechanism 3 transporting the printing paper P in a predetermined direction (front side on FIG. 1); and a control device 4 transport mechanism controlling various mechanisms of the printer 1 including the recording head 2 and the transport mechanism 3.

As shown in FIG. 1, the printer 1 has a printer-body (printer-body) 6 in a substantially rectangular parallelepiped shape, in which the recording head 2, the transport mechanism 3, and the control device 4, and so on are accommodated. As the recording head 2, a head which performs printing on the printing paper P by a known method such as ink-jet printing, laser printing or heat transfer printing is used. When a data recording medium 7 (see FIG. 2) in which image data are recorded is connected to the printer 1, this recording head 2 records an image of image data (image file) input from the data recording medium 7 on the printing paper P based on a command from the control device 4. Note that, in the following explanation, one image data (image file) refers to a set of data forming one sheet image.

A front side at a lower half portion of the printer-body 6 is partly opened, and in this opened portion, a paper feed tray 9 on which the printing paper P is put and a paper discharge tray 8 to which the printing paper P having an image recorded thereon is discharged are provided. The transport mechanism 3 transports the printing paper P put on the paper feed tray 9 to the recording head 2 in the printer-body 6 by a transporting roller rotary-driven by a motor, and discharges the printing paper P on which an image has been recorded by the recording head 2, to the paper discharge tray 8 provided in front of the printer-body 6.

On the front surface at the lower half portion of the printer-body 6, a cartridge loading section (cartridge installing section) 10 is provided at a side of the paper feed tray 9 and the paper discharge tray 8, and four ink cartridges 11 containing four color inks (yellow, magenta, cyan, and black) respectively are detachably loaded in the cartridge loading section 10.

An upper portion of the printer-body 6 is inclined toward a user staying at the front side of the sheet in FIG. 1, and a plurality of operation buttons 12 operated by a user are provided on an inclined surface 6a.

Figure 3A:
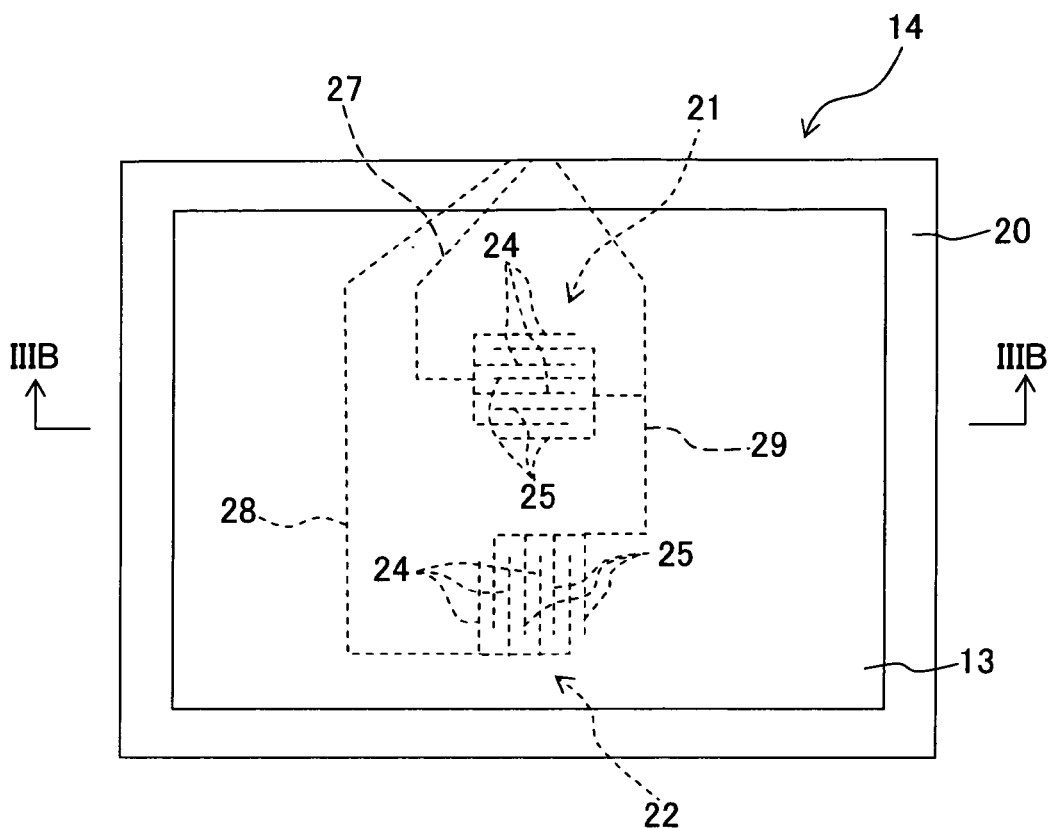
FIGS. 3A and 3B are views showing an input device.
Figure 3B:
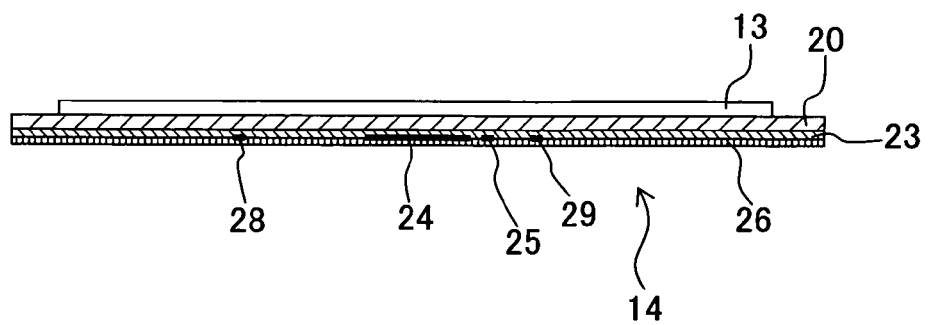

Further, the printer 1 is provided with an input device 14 (a bending-detection apparatus) having a sheet-shaped and flexible substrate (substrate) 20 and two bending-detection sections 21, 22 (a detecting mechanism) disposed on the surface of the substrate 20 detecting bending deformations of the substrate 20. FIG. 3A is a plan view of the input device 14, and FIG. 3B is a sectional view taken along IIIB-IIIB line of FIG. 3A. As shown in FIGS. 3A, 3B, on the surface of the substrate 20 of the input device 14, a display 13 (a display section) having flexibility as the whole is provided, and the display 13 is capable of being bending deformations integrally with the substrate 20. As an example of the display 13 like this, an electronic paper can be exemplified. The electronic paper has a thickness of about a few tenth of a millimeter as same as that of paper and it is possible to display and erase data by means of a voltage application. As shown in FIG. 1, note that the input device 14 and the display 13 are connected to the control device 4 (see FIG. 2) housed in the printer-body 6 via a cable 15.

When a user changes an image to be displayed on the display 13, the substrate 20 of the input device 14 is operated as if a user curves a paper. At this time, a bending deformation formed in the substrate 20 is detected in the two bending-detection sections 21, 22 provided on the substrate 20. The control device 4 controls the display 13 to change an image to be displayed on the display 13 based on an aspect of the bending deformation of the substrate 20 detected in the bending-detection sections 21, 22.

Hereinafter, the input device 14 is explained concretely. As shown in FIG. 3(a), the substrate 20 is formed in a rectangular shape in a plane view. As the substrate 20 with flexibility, a resin sheet made of synthetic materials such as polyimide, and so on, or a thin plate made of metals such as an aluminum alloy and stainless steel can be used.

On a rear surface (a surface not facing the display 13, a surface on a reverse side of the sheet in FIG. 3) of the substrate 20, the two bending-detection sections (a first bending-detection section 21 and a second bending-detection section 22) are provided. The two bending-detection sections 21, 22 are disposed in a longitudinal direction (a right and left direction on FIG. 3A) at a center area of the substrate 20 and arranged along a lateral direction (an up and down direction on FIG. 3(a). The bending-detection sections 21, 22, in this embodiment uses a machinery (distortion) electrical conversion function of a piezoelectric element. Namely, the respective bending-detection sections 21, 22 are provided with a piezoelectric layer 23 formed on a rear surface of the substrate 20 and two kinds of electrodes (first electrodes 24 and second electrodes 25) which are formed on a surface (rear face) of the piezoelectric layer 23 not facing the substrate 20 and extend parallel with spacing apart each other. As will be described later, a potential difference is generated between the first and the second electrodes 24, 25 in the bending-detection sections 21, 22 accompanying with deformations of the substrate 20. In this embodiment, the potential difference is detected in the control device 4. Namely, the control device 4 also functions as a sensor which detects a potential difference generated between the first and the second electrodes. As in this embodiment, it is not necessary that a sensor should be provided independently from the input device 14, and a sensor, which detects a potential difference generated between the first and the second electrodes can be integrally provided with the input device 14.

The piezoelectric layer 23 is made of a piezoelectric material whose main component is, for example, lead zirconate titanate (PZT) which is a solid solution of lead titanate and lead zirconate and is a ferroelectric, and the piezoelectric layer 23 is formed to cover the rear surface of the substrate 20 entirely. Namely, the piezoelectric layer 23 is common between the two bending-detection sections 21, 22. The piezoelectric layer 23 is formed on the substrate 20 by, for example, an aerosol deposition method, a sputtering method, and a sol gel method.

In the respective bending-detection sections 21, 22, on the rear surface (an opposite surface not facing the display 13) of the piezoelectric layer 23, the plurality of first electrodes 24 in a comb tooth shape which are extending parallel along one direction and conducting each other and the plurality of second electrodes 25 also in a comb tooth shape which are extending parallel to the plurality of first electrodes 24 and conducting each other are provided. Further, the plurality of first electrodes 24 and the plurality of second electrodes 25 are disposed alternately. These first electrodes 24 and second electrodes 25 are made of a conductive material such as, gold, copper, silver, palladium, platinum, or titanium, by means of a screen printing method, a vapor deposition method, and so on.

As shown in FIG. 3A, the extending direction of the electrodes (first electrodes 24 and second electrodes 25) in the first bending-detection section 21 is different from that in the second bending-detection section 22. More concretely, an extending direction of the electrodes, in the first bending-detection section 21, disposed at a slightly upper position to the center of the substrate 20 is parallel to the longitudinal direction of the substrate 20 having a rectangular shape. On the other hand, an extending direction of the electrodes, in the second bending-detection section 22, disposed at a slightly lower position to the center of the substrate 20 is parallel to the lateral direction (short-side direction) of the substrate 20. That is, the electrodes extending directions of the two bending-detection sections 21, 22 are perpendicularly intersecting to each other.

Note that in manufacturing steps, in the respective bending-detection sections 21, 22, a portion, of the piezoelectric layer 23, sandwiched between the first electrode 24 and the second electrode 25 is polarized in a direction from the second electrodes 25 toward the first electrodes 24 (a forward direction), because a low voltage (for example, 0V (a ground potential)) is applied to the first electrodes 24 and a high voltage (for example, 50V) is applied to the second electrodes 25 respectively. Note that the portion, of the piezoelectric layer 23, sandwiched between the first electrode 24 and the second electrode 25 also can be polarized in a reverse direction from the second electrodes 24 toward the first electrodes 25. That is, the portion, of the piezoelectric layer 23, sandwiched between the first electrode 24 and the second electrode 25 also can be polarized parallel or antiparallel (in the forward direction or in the reverse direction) to the direction from the first electrodes 24 toward the second electrodes 25.

As shown in FIG. 3A, a single line 27 is drawn out from the plurality of first electrodes 24 conducting each other in the bending-detection sections 21, and a single line 28 is also drawn out from the plurality of first electrodes 24 conducting each other in the bending-detection section 22, and these two lines 27, 28 for the first electrodes 24 are connected to the control device 4 (see FIG. 2). The plurality of second electrodes 25 in the first bending-detection section 21 and the plurality of second electrodes 25 in the second bending-detection section 22 are connected to a common line 29. The common line 29 is connected to a ground line provided on a side of the control section 4, and all the second electrodes 25 are always held at the ground potential via the common line 29.

As shown in FIG. 3(b), on the rear surface of the piezoelectric layer 23, an insulating layer 26 is formed to cover all the first electrodes 24 and the second electrodes 25 in the two bending-detection sections 21, 22. The insulating layer 26 can be made of a synthetic resin material having insulation property such as polyimide. In this manner, it is possible to avoid problems such as peeling and failure of the electrodes or a short circuit between the first electrodes 24 and the second electrodes 25 because the first electrodes 24 and the second electrodes 25 are covered with the insulating layer 26.

Next, operations of when the two bending-detection sections 21, 22 detect bending deformations of the substrate 20 will be explained with reference to FIGS. 4A to 7C. As shown in FIGS. 4A to 7C, a sign "+" shows a potential of the first electrodes 24 is a positive potential, a sign "−" shows a potential of the first electrodes 24 is a negative potential, and a sign "GND" shows a potential of the electrodes (the first electrodes 24 or the second electrodes 25) is the ground potential. FIGS. 4A, 5A, 6A, and 7A are plan views of the input device 14, FIGS. 4B, 5B, 6B, and 7B are sectional views taken along the IVB-IVB, VB-VB, VIB-VIB and VIIB-VIIB lines of FIGS. 4A, 5A, 6A, and 7A, respectively, and FIGS. 4C, 5C, 6C, and 7C are sectional views taken along the IVC-IVC, VC-VC, VIC-VIC and VIIC-VIIC lines of FIGS. 4A, 5A, 6A, and 7A, respectively.

When a bending deformation occurs in an area where the bending-detection sections 21, 22 of the substrate 20 are provided, and then a distortion (a deformation) is occurred in a portion between the first electrode 24 and the second electrode 25 of the piezoelectric layer 23, and an electric field (namely, a potential difference) between the first electrode 24 and the second electrode 25 is obtained depending on the distortion. The behavior will be explained further concretely in every aspect of the bending deformations of the substrate 20 separately.

As shown in FIGS. 4A to 5C, when the bending deformation occurs around an axis C1 parallel to the short-side direction in the substrate 20, the piezoelectric layer 23, together with the substrate 20, deforms to be convex toward the front side (upward) or the reverse side (downward). At this time, in the second bending-detection section 22, the portion between the first electrodes 24 and the second electrodes 25 of the lower side of the piezoelectric layer 23 is stretched or compressed along the direction perpendicular to the electrodes extending direction (the longitudinal direction of the substrate 20).

That is, as shown with a two-dot chain line in FIG. 4B, when the substrate 20 and the piezoelectric layer 23 are bent to be convex downward around the axis C1, the lower side of the piezoelectric layer 23 is stretched in a direction parallel to the polarization direction in the second bending-detection section 22 provided on the rear surface of the substrate 20. At this time, inside the piezoelectric layer 23, an electric field (namely, an electric field in a direction from the first electrodes 24 toward the second electrodes 25) in a reverse direction to the polarization direction is obtained, as the result, a positive potential (+) higher than a potential (the ground potential) of the second electrodes 25 is generated in the first electrodes 24.

Also, as shown with a two-dot chain line in FIG. 5B, when the substrate 20 and the piezoelectric layer 23 are bent to be convex upward around the axis C1, the lower side of the piezoelectric layer 23 is compressed in a direction parallel to the polarization direction in the second bending-detection section 22 provided on the rear surface of the substrate 20. At this time, inside the piezoelectric layer 23, an electric field (namely, an electric field in a direction from the first electrodes 25 toward the second electrodes 24) in the same direction as the polarization direction is obtained, as the result, a negative potential (−) lower than a potential (the ground potential) of the second electrodes 25 is generated in the first electrodes 24.

At this time, in the other first bending-detection section 21, as well, although a deformation (stretch or compression) occurs in the portion of the piezoelectric layer 23 sandwiched between the first electrodes 24 and the second electrodes 25, the deformation direction is parallel to the electrodes extending direction (the longitudinal direction of the substrate 20), and a different direction (an orthogonal direction) from the polarization direction of the piezoelectric layer 23 in the first bending-detection section 21. Therefore, a potential difference is less generated between the first electrode 24 and the second electrode 25 in the first bending-detection section 21.

As shown in FIGS. 6A to 7C, when a bending deformation is formed around an axis C2 parallel to the longitudinal direction in the substrate 20, the behavior of the second bending-detection section 22 explained above occurs in the first bending-detection section 21 in this time. That is, in the first bending-detection section 21, the portion between the first electrodes 24 and the second electrodes 25 on the lower side of the piezoelectric layer 23 is stretched or compressed along the direction (the short-side direction of the substrate 20) perpendicular to the electrodes extending direction.

That is, as shown with a two-dot chain line in FIG. 6C, when the substrate 20 and the piezoelectric layer 23 are bent to be convex downward around the axis C2, the lower side of the piezoelectric layer 23 is stretched in a direction parallel to the polarization direction in the first bending-detection section 21 provided on the rear surface of the substrate 20. At this time, inside the piezoelectric layer 23, an electric field (namely, an electric field in a direction from the first electrodes 24 toward the second electrodes 25) in the reverse direction to the polarization direction is obtained, as the result, a positive potential (+) higher than a potential (the ground potential) of the second electrodes 25 is generated in the first electrodes 24.

Also, as shown with a two-dot chain line in FIG. 7C, when the substrate 20 and the piezoelectric layer 23 are bent to be convex upward around the axis C2, the lower side of the piezoelectric layer 23 is compressed in a direction parallel to the polarization direction in the first bending-detection section 22 provided on the rear surface of the substrate 20. At this time, inside the piezoelectric layer 23, an electric field (namely, an electric field in a direction from the second electrodes 25 toward the first electrodes 24) in the same direction as the polarization direction is obtained, as the result, a negative potential (−) lower than a potential (the ground potential) of the second electrodes 25 is generated in the first electrodes 24.

At this time, in the second bending-detection section 22, as well, although a deformation (stretch or compression) occurs in the piezoelectric layer 23 between the first electrodes 24 and the second electrodes 25, the deformation direction is parallel to the electrodes extending direction (the short-side direction of the substrate 20), and a different direction (an orthogonal direction) from the polarization direction of the piezoelectric layer 23. Therefore, a potential difference is less generated between the first electrodes 24 and the second electrodes 25 in the second bending-detection section 22.

As has been described above, since the extending directions of the electrodes (the first electrodes 24 and the second electrodes 25) are different (perpendicularly intersecting) from each other between the two bending-detection sections 21, 22 provided on the substrate 20, the bending deformations of the substrate 20 around the two axes C1, C2 perpendicular to each other can be detected discriminatingly by means of the two bending-detection sections 21, 22.

Even if the respective bending-detection sections 21, 22 are not the ones that have the plurality of first electrodes 24 and the plurality of second electrodes 25 disposed alternately, but the ones that have the single first electrode 24 and the single second electrode 25 parallel to each other, whenever a potential change of the first electrode 24 of when the piezoelectric layer 23 between this one pair of the first electrode 24 and the second electrode 25 deforms is detected accurately at the control device 4 side, a bending deformation of the substrate 20 can be detected. However, if a potential change of the first electrode 24 is small, it is difficult to detect the potential change accurately, which causes a fear to occur erroneous detection. In order to prevent erroneous detection, it is effective to increase a detection sensitivity by narrowing an interval between the first electrode 24 and the second electrode 25 and making the potential change of the first electrode 24 of when a curvature is formed in the piezoelectric layer 23 large as much as possible. However, a range in which one bending-detection section can detect a bending deformation of the substrate 20 is to be very small.

However, in this embodiment, by which the plurality of first electrodes 24 and the plurality of second electrodes 25 extending in one same direction are disposed alternately on a same surface of the piezoelectric layer 23 in the respective bending-detection sections 21, 22, a plurality of electrode pairs each consisting of the first electrode 24 and the second electrode 25 exist. Accordingly, it is possible to detect a bending deformation of the substrate 20 formed within an area having a certain extent in one bending-detection section while increasing a detection sensitivity with shortening a distance between the first electrode 24 and the second electrode 25.

In this embodiment, as shown in FIG. 3B, the piezoelectric layer 23 is disposed on the opposite surface to the display 13 of the substrate 20. That is, the piezoelectric layer 23 and the display 13 are disposed on the opposite sides sandwiching the substrate 20. In this structure, compared with the case when the substrate 20, the piezoelectric layer 23, and the display 13 are stacked in this order (the case when the piezoelectric layer 23 exists between the substrate 20 and the display 13), a distance from a neutral line of a curvature of the three-layered structure to a lower surface of the piezoelectric layer 23 becomes large. This contributes a large distortion formed in the lower surface of the piezoelectric layer 23 when the substrate 20 is bent, and a potential generated in the first electrode 24 becomes large, as well, it makes it easier to detect a bending deformation of the substrate 20.

In the above-described bending deformations, the higher a bending speed (a bending speed) of the substrate 20 is, the larger a size of an electric field generated in the piezoelectric layer 23 becomes. Namely, if the second electrodes 25 are held at a constant potential (the ground potential), the higher a bendingbending speed of the substrate 20 is, the larger a potential (its absolute value) of the first electrodes 24 becomes. Accordingly, it is possible to detect even a difference of a bendingbending speed of bending deformations formed in the substrate 20 discriminatingly from the size of a potential (its absolute value) of the first electrodes 24.

Hereinbefore, the control device 4 can discriminatingly recognize the aspects of the plural bending deformations formed in the substrate 20 based on a voltage signal (a potential of the first electrodes 24) output respectively from the first bending-detection section 21 and the second bending-detection section 22.

In the printer 1 in this embodiment, when the substrate 20 of the input device 14 is bent at a predetermined aspect by a user as if paper is folded, a bending deformation formed in the substrate 20 thereat is detected in the two bending-detection sections 21, 22, and an image to be displayed on the display 13 is changed depending on the detected bending deformation (an image change process). A concrete content of this image change process will be described in detail in a next explanation of the control device 4.

Next, the electrical configuration of the printer 1, mainly the control device 4, will be explained in detail with reference to the block diagram in FIG. 2. The control device 4 is configured with a Central Processing Unit (CPU) as a central processing unit, a Read Only Memory (ROM) in which programs, data, and the like for controlling various mechanisms of the printer 1 are stored, a Random Access Memory (RAM) temporarily storing data processed by the CPU, and an input/output interface in which signals are input/output from/to an external apparatus, and the like.

As shown in FIG. 2, the control device 4 has the recording control section 30, the image data storage section 31 in which an image data input from the data recording medium 7 is stored, and the display control section 32 (a display control mechanism) controlling the display 13. In the data recording medium 7, a plurality of image data which are previously arranged in order based on a certain predetermined condition such as the names of data files (for example, in alphabetical order) and preparation dates of the image data are classified by image folders and recorded. The plurality of image data read from the data recording medium 7 are stored in the image data storage section 31 in the state when the data recording medium 7 is connected to the printer 1.

Storage devices, such as a USB memory and a memory card, which are connected when inserted in a slot or the like in the printer, external storage devices which are wire-connected by a cable or external storage devices which are wirelessly connected to the control device 4 correspond to the data recording medium 7 storing the image data. The image data stored in the data recording medium 7 may be not only a still image data photographed by a digital camera, but also a move data photographed by a digital video camera. Herein, the movie data is a set of a plurality of temporally subsequent still image data. When the movie data is input from the data recording medium 7, a plurality of still image data are extracted from the input movie data in the control device 4. Consequently, a part of these plural still image data is to be displayed on the display 13, or the still image is to be printed on the printing paper P.

The recording control section 30 is configured such that an image of image data selected by a user is printed on the printing paper P by controlling the recording head 2 and the transport mechanism 3 respectively with reference to the data stored in the image data storage section 31. Further, the display control section 32 controls the display 13 to display a status of the printer 1 (a state where image recording is underway, a standby state, or the like), an error message, and so on, thereby notifying these pieces information to the user.

Further, the display control section 32 is provided with a function to change an image to be displayed on the display 13 depending on an aspect of a bending deformation of the substrate 20 detected in the two bending-detection sections 21, 22 when the substrate 20 of the input device 14 is bent by a user. Note that "to change an image to be displayed on the display 13" means that a part or a whole of the image, which is displayed on the whole screen of the display 13 is changed. Accordingly, it also means not only switching an image of an image date being displayed currently to an image of another image data, but also performing an image process such as enlargement or reduction to the image being displayed currently.

Note that the recording control section 30, the image data storage section 31, and the display control section 32 are realized by the CPU, the ROM, the RAM, and so on configuring the control device 4. In other words, various programs such as a control program for the recording head 2 and the transport mechanism 3 and a program for changing an image to be displayed on the display 13 are stored in the ROM of the control device 4, and the program stored in the ROM is executed in the CPU of the control device 4, which leads the respective functions of the recording control section 30, the image data storage section 31, and the display control section 32 to be realized.

Image Change Process

The image change process executed by the display control section 32, when the substrate 20 of the input device 14 is bent by a user will be explained.

As described before, the printer 1 in this embodiment can discriminatingly detect aspects of plural bending deformations in the substrate 20 occurred when the substrate 20 is performed a curvature operation by the user in the two bending-detection sections 21, 22 provided on the substrate 20. As shown in FIGS. 8A and 8B, the contents of six kinds of the image change processes related to enlargement/reduction of an image and an image switching are assigned beforehand to six kinds of bending deformations detected discriminatingly in the two bending-detection sections 21, 22 (Items A to F).

Enlargement/Reduction of Images

As shown in FIGS. 4A to 4C, when the substrate 20 having a rectangular sheet shape is bent to be convex downward (a reverse side from the user's view) around the axis C1 parallel to the short-side direction by the user (Item A in FIGS. 8A and 8B), the lower side of the piezoelectric layer 23 is stretched in the longitudinal direction of the substrate 20. And then, in the area between the first electrode 24 and the second electrode 25 in the second bending-detection section 22, an electric field in a reverse direction (a direction from the first electrodes 24 toward the second electrodes 25) to the polarization direction is obtained in the piezoelectric layer 23, which leads to generate a positive potential in the first electrodes 24 in the second bending-detection section 22. With receiving this signal, the display control section 32 judges that the substrate 20 is bent downward to be convex around the axis C1, therefore, the display control section 32 displays a reduced image of which the image being displayed currently is further reduced on the display 13.

As shown in FIGS. 5A to 5C, when the substrate 20 is bent to be convex upward (a front side from the user's view) around the axis C1 parallel to the short-side direction (Item B in FIGS. 8A and 8B), the lower side of the piezoelectric layer 23 is compressed in the longitudinal direction of the substrate 20. And then, in the area between the first electrode 24 and the second electrode 25 in the second bending-detection section 22, an electric field in the same direction (the direction from the second electrodes 25 toward the first electrodes 24) as the polarization direction is obtained in the piezoelectric layer 23, which leads to generate a negative potential in the first electrodes 24. With receiving this signal, the display control section 32 judges that the substrate 20 is bent upward to be convex around the axis C1, therefore, the display control section 32 displays an enlarged image of which the center portion of the image being displayed currently is enlarged on the display 13.

That is, when the substrate 20 is bent toward the reverse side from the user's view (downward) to be convex by the user as if the substrate 20 goes away from the user, the display control section 32 reduces the image being displayed on the display 13. On the other hand, when the substrate 20 is bent toward the front side from the user's view (upward) to be convex as if the substrate 20 comes to the user, the display control section 32 enlarges the image being displayed on the display 13. From this structure, the operation, of which the substrate 20 is neared corresponds to enlargement of an image, and the action, of which the substrate 20 is made to be away corresponds to reduction of an image, therefore, there is an advantage that the user can sensuously learn the curvature operations of the substrate 20 in images enlarged/reduced.

Herein, it is not necessary that an image data (it is also called a display image data) of an image displayed on the display 13 should be the same as an image data (it is also called an original image data) in the image data storage section 31 input from the data recording medium 7. For example, in the case of the original image data being a high resolution image data for printing, the display image data can be created as an image data of which the original image data resolution is reduced. As described above, when the user instructs enlargement, reduction of the image being displayed, image data of an enlarged image and a reduced image can be created from the display image data, and then the enlarged (or reduced) image can be displayed on the display. Alternatively, image data of an enlarged image and a reduced image can be created from the original image data every time the user instructs, and then the enlarged (or reduced) image can be displayed on the display. As will be described later, when an enlarged image and a reduced image can be printed, it is necessary to create an image data for printing corresponding to an enlarged image and a reduced image to be an object to be printed. In the case, every time the user instructs enlargement (reduction) of an image, the display image data and the image date for printing for the enlarged (reduced) image corresponding to it can be created. Or when the user instructs enlargement (reduction) of an image, the display image data for the enlarged (reduced) image corresponding to it can be created, and then when the user instructs printing, the image data for printing corresponding to the image being displayed at this moment can be created.

Switching Images (Forward-Feed/Backward-Feed of Images)

As shown in FIGS. 6A to 6C, when the substrate 20 having a rectangular sheet shape is bent to be convex downward (a reverse side from the user's view) around the axis C2 parallel to the longitudinal direction by the user, the lower side of the piezoelectric layer 23 is stretched in the short-side direction of the substrate 20. Herein in the case when the substrate 20 is bent to be convex downward at a relatively slow speed (Item C in FIGS. 8A and 8B), in the area between the first electrode 24 and the second electrode 25 in the first bending-detection section 21, a weak electric field in a reverse direction (a direction from the first electrodes 24 toward the second electrodes 25) to the polarization direction is obtained in the piezoelectric layer 23, which leads to generate a relatively small positive potential, of which an absolute value of the potential is a predetermined value or less in the first electrodes 24 in the first bending-detection section 21.

With receiving the signal, the display control section 32 judges that the substrate 20 is bent downward to be convex around the axis C1 at a slow speed. It selects an image data immediately after rather than the data currently being displayed on the display 13 out of plural image data stored in the state of being arranged in order in the image data storage section 31, and then switches an image to be displayed on the display 13 to the image of the selected image data.

As shown in FIGS. 7A to 7C, when the substrate 20 having a rectangular sheet shape is bent to be convex upward (a front side from the user's view) around the axis C2 parallel to the longitudinal direction by the user, the lower side of the piezoelectric layer 23 is compressed in the short-side direction of the substrate 20. Herein when the substrate 20 is bent to be convex upward at a relatively slow speed (Item D in FIGS. 8A and 8B), in the area between the first electrode 24 and the second electrode 25 in the first bending-detection section 21, a weak electric field in the same direction (a direction from the second electrodes 25 toward the first electrodes 24) as the polarization direction is obtained in the piezoelectric layer 23, which leads to generate a relatively small negative potential, of which an absolute value of the potential is a predetermined value or less in the first electrodes 24 in the first bending-detection section 21.

With receiving the signal, the display control section 32 judges that the substrate 20 is bent upward to be convex around the axis C2 at a slow speed. At this moment, the display control section 32 selects an image data immediately before rather than the data being currently displayed on the display 13 among the ordered image data stored in the image data storage section 31, and then switches an image to be displayed on the display 13 to the image of the selected image data.

Further, in FIGS. 6A to 7C, the higher the bending speed of when the substrate 20 is bent to be convex downward or upward is, the larger an electric field obtained in the piezoelectric layer 23 between the first electrode 24 and the second electrode 25 in the first bending-detection section 21, which leads an absolute value of a potential in the first electrodes 24 to be large. Accordingly, the display control section 32 judges that the substrate 20 is bent at a considerably fast speed when the absolute value of the potential in the first electrodes 24 is larger than a predetermined value (Items E, F in FIGS. 8A and 8B). At this time, the display control section 32 makes the display 13 perform forward-feed/backward-feed of display images at a far rougher interval (a larger interval) than the previous processes (Items C, D in FIGS. 8A and 8B).

That is, when the display control section 32 judges that the substrate 20 is bent downward to be convex at a considerably fast speed, it switches an image to be displayed on the display 13 to the image immediately five images after rather than the image being currently displayed. Conversely, when it judges that the substrate 20 is bent upward to be convex at a considerably fast speed, the display control section 32 switches an image to be displayed on the display 13 to the image immediately five images before rather than the image being currently displayed.

That is, when the user knows that the image being displayed currently is an image considerably away in order from the desired image to be displayed, it is possible to forward-feed/backward-feed every five images by bending the substrate 20 at a fast speed as if the image to be displayed on the display 13 nears the desired image for a short time. After that, as the display image is getting closer to the desired image, it is possible to forward-feed/backward-feed every one image by bending the substrate 20 at a slow speed while confirming whether or not the displayed image is the desired image.

As above, a command to record the image is input by which the operation button 12 (see FIG. 1) and the like, are operated by the user after the desired image is displayed on the display 13. Consequently, the recording control section 30 controls the recording head 2 and the transport mechanism 3 to record the image being displayed currently on the display 13 on the printing paper P.

According to the printer 1 in this embodiment described above, the following effects can be obtained. When a bending deformation is occurred in the sheet-shaped substrate 20 having flexibility as if a user curves paper, the bending deformation in the substrate 20 is detected in the two bending-detection sections 21, 22, and further, based on the detected bending deformation, an image to be displayed on the display 13 is changed in the display control section 32. According to the configuration, only a simple operation getting the substrate 20 bent makes it possible to perform enlargement/reduction of images and switching images (forward-feed/backward-feed). Therefore, in order to change an image to be displayed on the display 13, a complicated operation using the plural operation buttons 12 and the like is not required, and even a user not good at operating devices can easily change an image to be displayed on the display 13.

And also, the bending-detection sections 21, 22 have the plurality of first electrodes 24 and the plurality of second electrodes 25 disposed alternatively on one surface (a lower surface) of the piezoelectric layer 23. When the substrate 20 is bent by the user, and then a distortion of compression or stretch is occurred in a direction perpendicular to an electrodes extending direction on the one side of the piezoelectric layer 23, a potential difference between the first electrode 24 and the second electrode 25 is obtained depending the distortion. This leads a bending deformation in the substrate 20 to be detected. Further, the two bending-detection sections 21, 22 are provided on the substrate 20, electrodes (the first electrodes 24 and the second electrodes 25) extending directions between these two bending-detection section 21, 22 are different. Therefore, two kinds of bending deformations occurred in the substrate 20, whose curvature directions are different from each other, can be detected respectively in the two bending-detection section 21, 22.

Next, modified forms in which this embodiment described above is variously modified will be explained. Components having substantially the same configuration as those of the above first embodiment will be denoted by the same reference numerals and symbols, and explanation thereof will be omitted when appropriate.

The configurations, the numerals, and the positions on the substrate surface, and the like of a bending-detection section to detect a bending deformation of a substrate are not limited to the above-described embodiment, for example, the following modifications are possible as below.

First Modification

Figure 9:
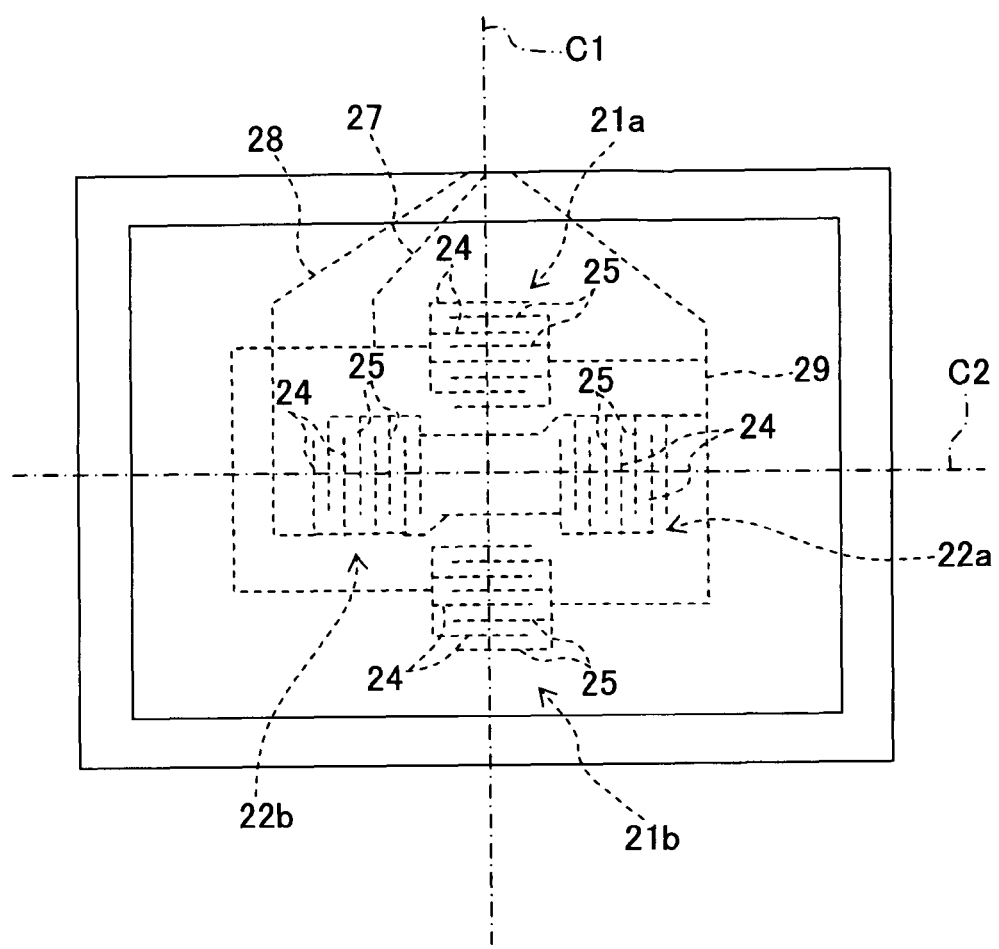
FIG. 9 is a plan view of an input device of the first modified form.

In order to detect overall bending deformations of the substrate 20 securely, a plurality of the first bending-detection sections 21 and the second bending-detection sections 22, whose electrodes extending directions are different from each other, can be provided respectively on the substrate 20, and further, as shown in FIG. 9, the plural (two in FIG. 9) first bending-detection sections 21 (electrodes extending direction: longitudinal direction of the substrate 20) and the plural (two in FIG. 9) second bending-detection sections 22 (electrodes extending direction: short-side direction of the substrate 20) can be disposed on the center side of the substrate 20.

In the first modified form, two first bending-detection sections 21a, 21b together are provided to detect overall bending deformations of the substrate 20 around the axis C2 parallel to the longitudinal direction of the substrate 20, and two second bending-detection sections 22a, 22b together are provided to detect overall bending deformations of the substrate 20 around the axis C1 parallel to the short-side direction of the substrate 20. Therefore, it is not necessary that a wire to detect a potential of the first electrodes 24 should be independent between the two first bending-detection sections 21a and 21b, or between the two second bending-detection sections 22a and 22b. Accordingly, as shown in FIG. 9, the first electrodes 24 of the two first bending-detection sections 21a, 21b can be conducted each other and connected to the common wire 27, and also the first electrodes 24 of the two second bending-detection sections 22a and 22b can be conducted each other and connected to the common wire 28.

Second Modification

Figure 10:
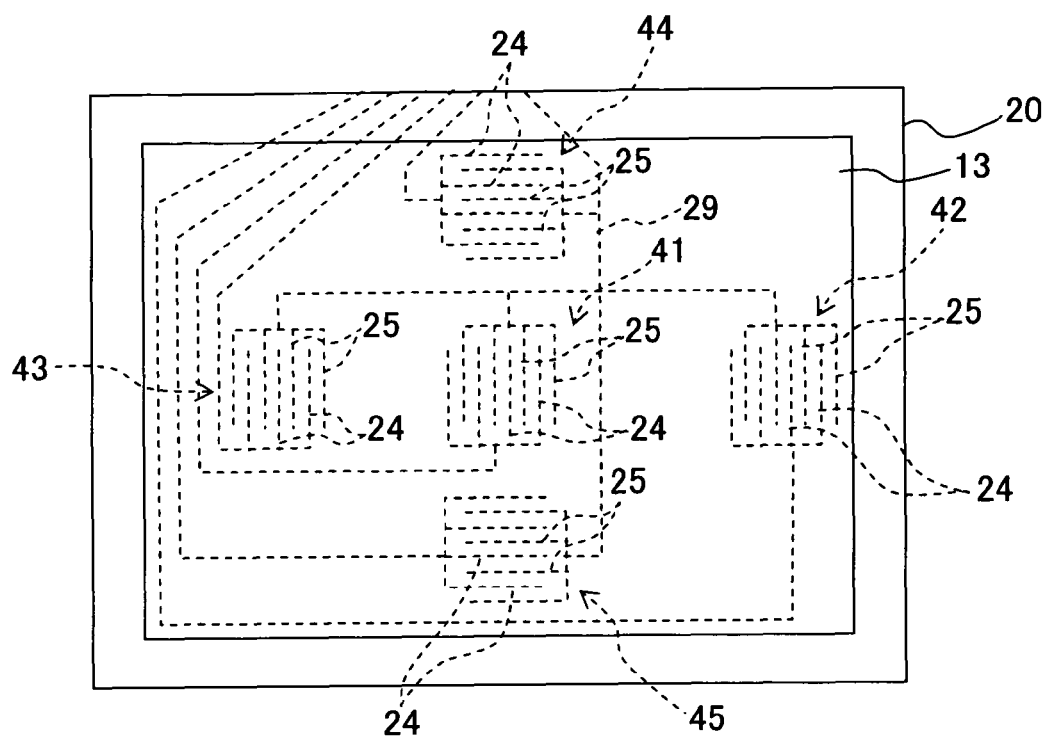
FIG. 10 is a plan view of an input device of the second modified form.

As shown in FIG. 10, five bending-detection sections 41, 42, 43, 44, and 45 can be provided respectively on the center portion of the substrate 20 and the four sides around thereof, at five portions in total. In the second modified form, in the three bending-detection sections 41, 42, and 43, arranged right and left at the center portion along the longitudinal direction in the drawing out of the five bending-detection sections 41 to 45 provided on the substrate, the extending directions of the first electrodes 24 and the second electrodes 25 are parallel to the short-side direction of the substrate 20. On the other hand, the two bending-detection sections 44, 45 provided respectively at both sides longitudinally in the drawing, the extending directions of the first electrodes 24 and the second electrodes 25 are parallel to the longitudinal direction of the substrate 20. While independent wires are drawn out of the first electrodes 24 in the five bending-detection sections 41 to 45, the second electrodes 25 in the five bending-detection sections 41 to 45 are connected to the common wire 29.

Accordingly, a bending deformation in the substrate 20 around the axis parallel to the short-side direction thereof is detected in the three bending-detection sections 41, 42, and 43 disposed at the center portion along the longitudinal direction of the substrate 20, and a bending deformation of the substrate 20 around the axis parallel to the longitudinal direction thereof is detected in the longitudinal two bending-detection sections 44, 45.

Further, the five bending-detection sections 41 to 45 are respectively disposed in different areas on the surface of the substrate 20, therefore, when only a portion of the substrate 20 is bent by a user, the bending deformation locally occurred in the portion can be detected. For example, when the right end portion of the substrate 20 is bent around the axis parallel to the short-side direction of the substrate 20, the bending deformation locally occurred in the right end portion is detected in the right side bending-detection section 42. In this manner, not only the curvature direction but also the curvature position of when being bent locally can be detected. That is, aspects of bending deformations of the substrate 20 can be discriminatingly detected in further detail compared with the above-described embodiment, consequently, it makes it possible to assign a lot of processes to the aspects of the bending deformations detected discriminatingly.

One example of the assignments of the processes will be explained referring to FIGS. 11A and 11B. Note that "bending positions" in FIG. 11A indicate the positions where the substrate 20 is bent by a user. In FIGS. 11A, 11B, when a potion of the substrate 20 is bent locally, the display control section 32 enlarges/reduces an image being displayed on the display 13, mainly the portion corresponding to the disposed area of the bending-detection sections 41 to 45 having detected the bending deformation of the substrate 20.

As indicated in Item C in FIGS. 11A and 11B, for example, the right end portion of the substrate 20 is bent downward (the reverse side) to be convex by a user in the state of an image being displayed on the display 13, only the first electrodes 24 in the bending-detection section 42 provided on the right end portion of the substrate 20 become a positive potential, the potentials of the first electrodes 24 in the other bending-detection sections 41, 43, 44, and 45 remain the ground potential. Accordingly, with receiving the signals output from the bending-detection sections 41 to 45, the display control section 32 judges that the right end portion of the substrate 20 is locally bent downward to be convex. At this time, in the case when the image being displayed on the display 13 is an image in a standard state (an image in the state of not being enlarged), the display control section 32 displays an image of which the right end portion of the image is mainly enlarged corresponding to the disposed area of the bending-detection section 42 on the display 13. And in the case when the image being displayed currently on the display 13 is an image whose portion has been already enlarged, the display control section 32 changes the enlarged position to the right end portion (namely, the display image on the display 13 is switched to the image whose right end portion is enlarged).

Conversely, as indicated in Item D in FIGS. 11A and 11B, the right end portion of the substrate 20 is bent upward (the front side) to be convex by a user, only the first electrodes 24 in the bending-detection section 42 provided on the right end portion of the substrate 20 become a negative potential, the potentials of the first electrodes 24 in the other bending-detection sections 41, 43, 44, and 45 remain the ground potential. Accordingly, with receiving the signals output from the bending-detection sections 41 to 45, the display control section 32 judges that the right end portion of the substrate 20 is locally bent upward to be convex. At this time, the display control section 32 displays an image of which the right end portion is mainly reduced corresponding to the disposed area of the bending-detection section 42 on the display 13.

In the case when the center portion, the left end portion, the upper end portion and the lower end portion of the substrate 20 are respectively bent downward or upward to be convex as well, similar to the above-described case when the right end portion of the substrate 20 is bent, enlargement or reduction of an image is performed mainly at the portion corresponding to the curvature position of the substrate 20.

Consequently, in the assignments indicated in FIGS 11A and 11B, when the substrate 20 is locally bent in an area where one of the five bending-detection sections 41 to 45 is provided, a user can designate that an image is enlarged or reduced mainly at which portion of an image being displayed on the display 13.

When it is detected that the bending-detection sections 42 to 45 are bent upward, instead of displaying the enlarged images of which the right side, the left side, the upper side, and the lower side of the image respectively are based and further enlarged, the image can be shifted toward the right side, the left side, the upper side, and the lower side. Such an operation is effective, for example in the case when an image data such as a map or the like is stored in the image data storage section 31, and the portion thereof is enlarged and displayed on the display 13. With a GPS receiver provided in the control device 4, it is possible to display a current position-based enlarged map on the display 13. In such a case, by the upper end portion of the substrate 20 being bent, for example, the range of the map being displayed on the display 13 can be shifted upward, and a user can shift the range of the map displayed on the display 13 intuitively. Note that an image to be displayed on the display 13 is not limited to map images, and the similar operation can be performed even in arbitrary images.

Third Modification

Figure 12:
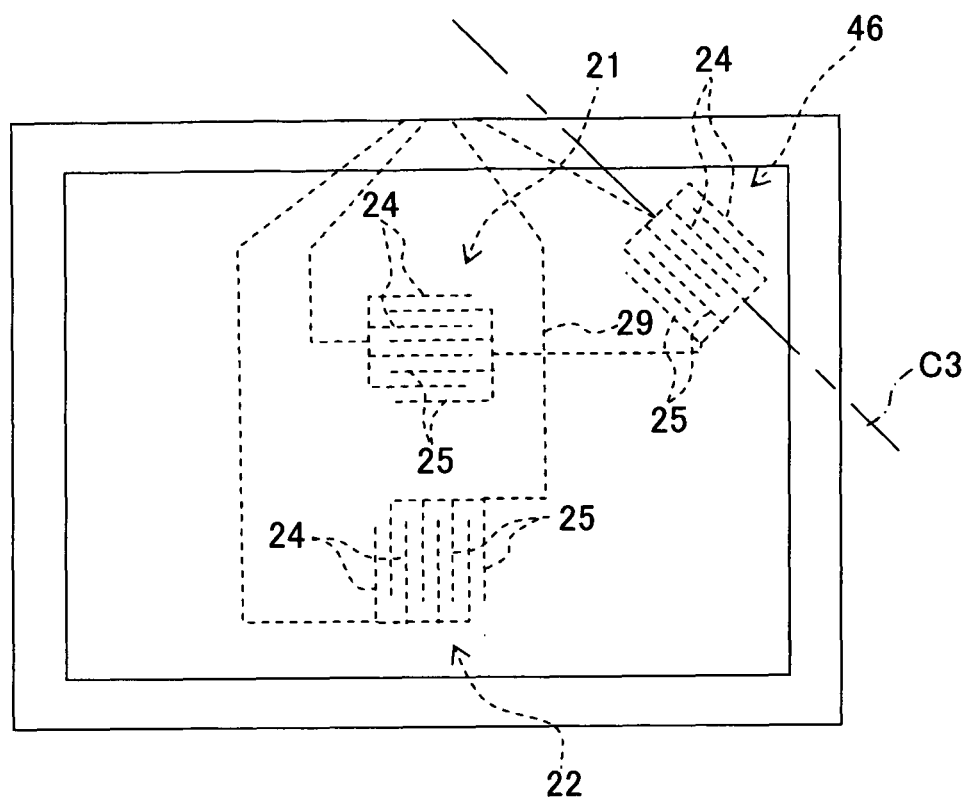
FIG. 12 is a plan view of an input device of the third modified form.

As shown in FIG. 12, it can be configured such that the bending-detection section (a third bending-detection section 46) is provided on an area at the right upper corner of the rectangular shaped substrate 20 as well, and a bending deformation at the right upper corner of the substrate 20 is detected in the third bending-detection section 46. The extending directions of the first electrodes 24 and the second electrodes 25 in the third bending-detection section 46 are the directions that are inclined at 45 degrees in a right-handed direction (a clockwise direction) to the longitudinal direction of the substrate 20 (the electrodes extending direction of the first bending-detection section 21), and at 45 degrees in a left-handed direction (a counterclockwise direction) to the short-side direction of the substrate 20 (the electrodes extending direction of the second bending-detection section 22) A wire independent from the first bending-detection section 21 and the second bending-detection section 22 is drawn out of the first electrodes 24 in the third bending-detection section 46, on the other hand, the second electrodes 25 in the third bending-detection section 46 are connected to the wire 29 common with the second electrodes 25 in the first bending-detection section 21 and the second bending-detection section 22.

With the third bending-detection section 46 provided at the right upper corner of the substrate 20, when the right upper corner of the substrate 20 is bent downward (the reverse side) or upward (the front side) based on an axis C3 parallel to the electrodes extending direction as if to fold an end of paper, a potential of the first electrodes 24 of the third bending-detection section 46 becomes either a positive potential or a negative potential, which makes it possible that the display control section 32 can recognize that the right upper end of the substrate 20 is bent.

Further, in the third modified form, as indicated in FIGS. 13A and 13B, the bending deformation of the right upper corner in the substrate 20 detected in the third bending-detection section 46 is considered as a deformation of a different aspect from a bending deformation to change an image to be displayed on the display 13. Accordingly, a different process from the above-described image change process is assigned to the bending deformation of the right upper corner.

In FIGS. 13A and 13B, since the image change processes of Items A to F are similar to FIGS. 8A, 8B of the above-described embodiments, the explanations thereof are omitted. Meanwhile, as indicated in Item G in FIGS. 13A, 13B, when the right upper corner of the substrate 20 is bent downward (the reverse side) to be convex around the axis C3 by a user, and then the first electrodes 24 of the third bending-detection section 46 become a positive potential, the recording control section 30 judges the bending deformation occurred in the substrate 20 as not the bending deformation to change an image to be displayed on the display 13 but the bending deformation to record an image, which lets the recording head 2 record an image being displayed currently on the display 13 on the printing paper P. As indicated in Item H in FIGS. 13A and 13B, when the right upper corner of the substrate 20 is bent upward (the front side) to be convex, and then the first electrodes 24 in the third bending-detection section 46 become a negative potential once after a recording command of an image is given as the descried procedure above, the recording control section 30 lets the recording head 2 cancel recording an image.

In the third modification, forming a bending deformation, which is different from the case of changing an image to be displayed on the display 13, in the substrate 20 enables the recording head 2 to record an image being displayed on the display 13 on the printing paper P. Therefore, in order to instruct recording of images, a user does not need to operate an operation section (the operation button 12 and the like shown in FIG. 1) different from the input device 14. And also, by bending the right upper corner of the substrate 20 as if to fold an end of paper to select a predetermined page of a book and a booklet, an image being displayed currently on the display 13 is selected and recorded, or the recording command which has been given once can be cancelled. This leads to memorize the curvature operation of the substrate 20 in recording images sensuously.

Fourth Modification

Figure 14A:
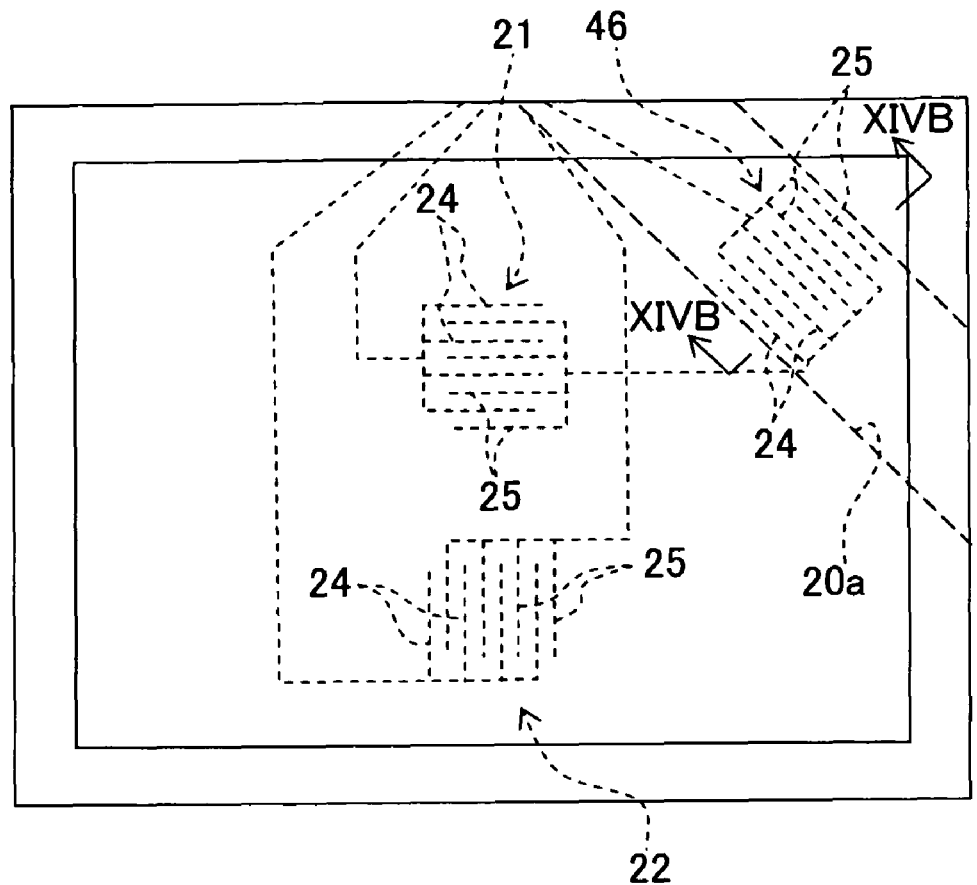
FIGS. 14A and 14B are views showing an input device of the fourth modified form.
Figure 14B:
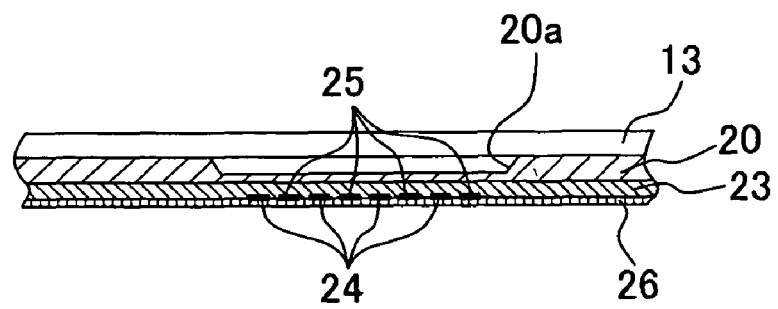

Thickness of the substrate can be locally thin in an area where the bending-detection section is disposed. For example, as shown in FIGS. 14A, 14B, in the area where the first electrodes 24 and the second electrodes 25 in the third bending-detection section 46 are provided in the second modification, a groove 20a parallel to the electrodes extending direction of the third bending-detection section 46 is made in an upper side of the substrate 20. Consequently, the thickness of the substrate 20 in the area can be locally thin. In this case, the substrate 20 can be deformed easily in the disposed area of the third bending-detection section 46 (the right upper corner), and then a potential in the first electrodes 24, which is obtained when the substrate 20 is bent, becomes large. This contributes to detect a bending deformation in the substrate 20 easily. The thickness of the substrate 20 can be locally thin in the disposed areas of the first bending-detection section 21 and the second bending-detection section 22.

Fifth Modification

Figure 15A:
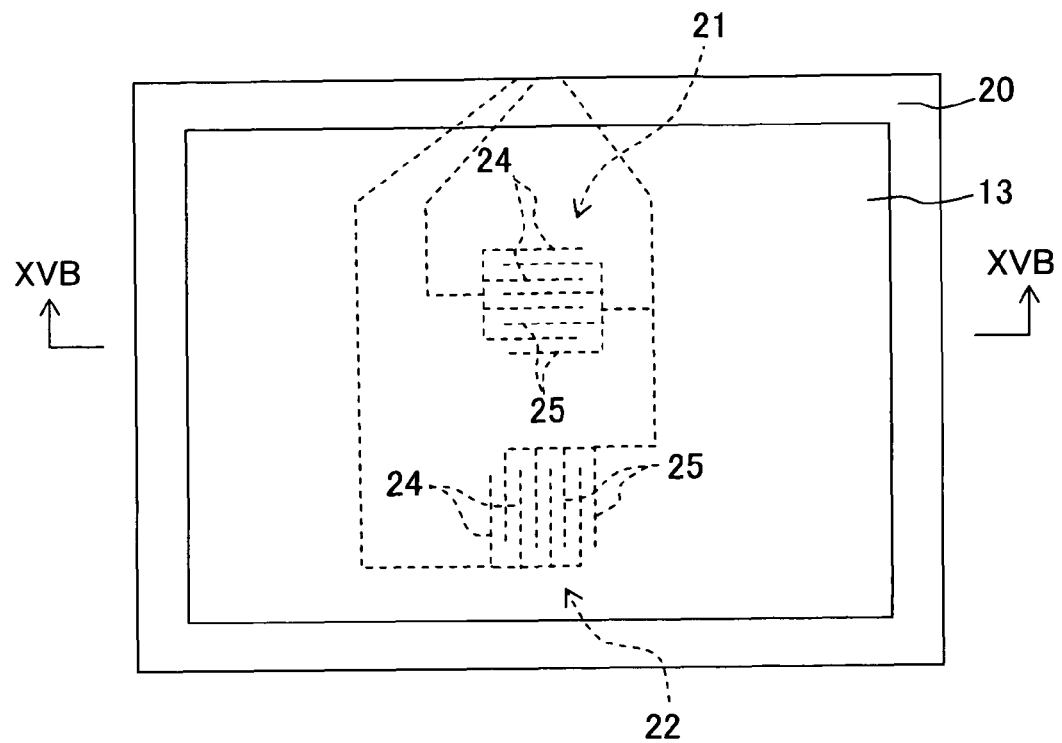
FIGS. 15A and 15B are views showing an input device of the fifth modified form.
Figure 15B:
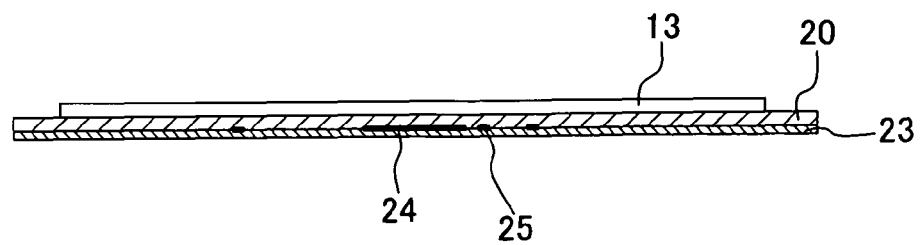

In the above-described embodiment, since the first electrodes 24 and the second electrodes 25 in the bending-detection sections 21, 22 are disposed on the opposite side to the substrate of the piezoelectric layer 23, as shown in FIGS. 15A, 15B, the first electrodes 24 and the second electrodes 25 in the bending-detection sections 21, 22 can be formed on a surface, of the piezoelectric layer 23, facing the substrate 20. In this case, however, it is necessary that at least the lower side of the substrate 20 should have insulating performance by such as the substrate 20 composed of insulative materials, so that the first electrodes 24 and the second electrodes 25 do not conduct each other. In this form as well, the insulating layer 26 (see FIG. 3B) on the rear surface of the piezoelectric layer 23, which is necessary to cover the first electrodes 24 and the second electrodes 25 in the previous form, is not necessary.

Sixth Modification

In the above-described embodiment and the modifications thereof, as the image change processes performed in the display control section 32, the image enlargement/reduction process and the image switching process are assigned to the aspects of the various bending deformations in the substrate 20 detected in the bending-detection sections. However, it is possible to assign processes except these to the detected bending deformations in the substrate 20.

Figure 16A:
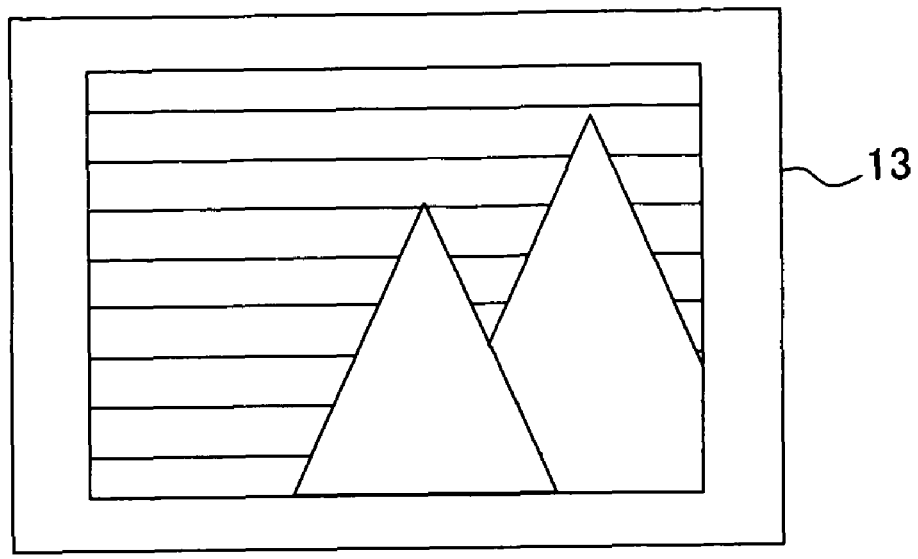
FIGS. 16A and 16B are explanatory views relating to changing of the number of the display images on a display.
Figure 16B:
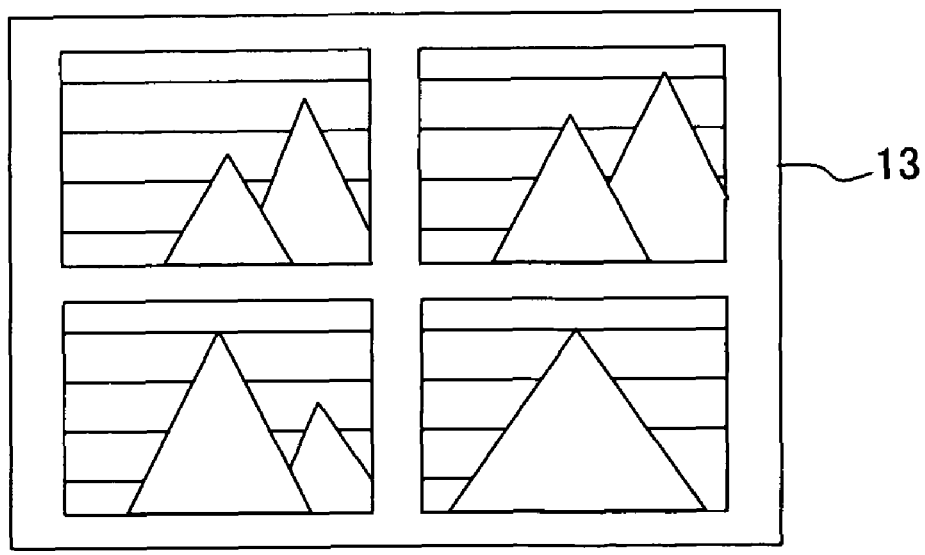

Generally, for example, the display control section 32 controlling the display 13 can display one image on the display 13 as shown in FIG. 16A. However, as shown in FIG. 16B, it is also possible to display a list-image (thumbnail images) including a plurality (for example, 4 pieces) of reduced images (thumbnail images) on the display 13. Then, when a bending deformation in the substrate 20 is detected in the bending-detection section, the display control section 32 can also change the number of the images to be list-displayed on the display 13.

Regarding the assignment of the image change process in the sixth modification, the case, of which the input device in the above-described second modification with the five bending-detection sections 41 to 45 provided on the substrate 20 (see FIG. 10) is adopted, will be explained as an example. In the input device in FIG. 10 as described in the explanation of the first modification, the bending deformations at the center portion, the right end portion, the left end portion, the upper end portion, and the lower end portion, five portions in total, of the substrate 20 can be detected independently in the five bending-detection sections 41 to 45. The process contents of the image change processes, assigned to the bending deformations in the substrate 20 detected in the five bending-detection sections 41 to 45, and that the display control section 32 lets the display 13 perform, are indicated in FIGS. 17A and 17B.

When the center portion of the substrate 20 is bent downward (the reverse side) to be convex by a user (Item A in FIGS. 17A and 17B), the display control section 32 increases the number of the list-displayed images on the display 13. When the center portion of the substrate 20 is bent upward (the front side) to be convex by a user (Item B in FIGS. 17A and 17B), the display control section 32 decreases the number of the list-displayed images on the display 13. When the substrate 20 is bent downward to be convex, for example, the state of the display 13 is switched from the standard display state where one image is displayed overall as shown in FIG. 16A to the state where four reduced images (the thumbnail images) are displayed as shown in FIG. 16B. Conversely, when the substrate 20 is bent upward to be convex, the thumbnail image display state in FIG. 16B is switched to the standard display state in FIG. 16B. When the substrate 20 is bent downward to be convex so as to increase the number of the images more in the state of the four thumbnail images displayed, the number of the thumbnail images to list-display can be increased from four or more (for example, eight pieces).

When the right end portion of the substrate 20 is bent downward to be convex by a user in the state where plural images (the thumbnail images) are list-displayed on the display 13 (Item C in FIGS. 17A and 17B), the display control section 32 newly selects the image positioned right of the image being selected currently out of the list-displayed plural images on the display 13. Namely, the selecting image is changed to the right image. Note that "the image being selected" indicates the state where one of the list-displayed images on the display 13 is differentiated from the other images list-displayed by such as surrounded with a thick frame, brightness increased or blinking to determine an image to be an object for recording images and performing image processes.

When the left end portion, the upper end portion, and the lower end portion of the substrate 20 are bent respectively, the left, the upper, and the lower images positioned to the image being selected currently among the plural images list-displayed on the display 13 are respectively selected (Items D, E, and F in FIGS. 17A and 17B).

After that, when recording of the selected image is instructed by such as the operation button 12 (see FIG. 1) operated by a user, the recording control section 30 lets the recording head 2 record the selected image on the printing paper P.

Except the process such as changing of the number of the list-display images, it is also possible to assign various processes such as rotation of an image being displayed currently, changing of dark and light, a tone, or a contrast of images, and the like to bending deformations in the substrate 20.

It is not always necessary that the display displaying an image should be provided integrally with the substrate. For example, it can be configured such that the display is disposed on a side of the operation button 12 on the inclined surface 6a of the printer body 6 (see FIG. 1), and a user performs a bending operation for the substrate of the input device while looking at the display provided on the printer body 6. The input device provided with the substrate and the plural bending-detection sections can be the one to be used not only for changing images on the display but also for setting inputting various items related to the printer such as setting regarding a sound volume, a sound effect, and a melody in operation of the printer and the like.

Hereinbefore, as the embodiment of the present invention, the examples applied to the input device connected to the printer and performed the curvature operations by a user have been explained, however, objects applicable to the bending-detection apparatus of the present invention are not limited to this. That is, being the ones required detecting bending deformations in a sheet-shaped substrate occurred by external forces and the like acted, regardless of objects of bending-detection, the bending-detection apparatus of the present invention is allowed to be applied.

In the above-described embodiment, although the piezoelectric layer is polarized parallel to the direction from the first electrodes toward to the second electrodes in advance, it can not always be polarized in advance. But in this case, before using the bending-detection apparatus, the operation for polarizing the piezoelectric layer is required, for example by such as applying a predetermined voltage to the first, the second electrodes by a user. And also, in the above-described embodiment, curvatures in the substrate mainly in the direction perpendicular to the extending direction of the first, the second electrodes are detected. However, the bending-detection apparatus of the present invention has the plural (curvature) detecting sections whose electrodes extending directions are different from each other. Potential differences generated simultaneously among these plurality of detecting sections are respectively detected, based on the ratio of the size of the potential difference generated in the detecting section, and then curvatures in arbitrary directions of the substrate, which are not limited to the direction perpendicular to the electrodes extending direction, can be detected. In other words, it is possible to obtain in which direction the substrate is bent.

Note that in FIGS. 8A, 11B, 13B and 17B corresponding to the above-described embodiment and modifications, the indication of "GND" does not necessarily mean that the electric potential difference is 0 (zero). For example, it is also allowable that: (1) a case that the potential difference is not more than a predetermined threshold value is considered as "GND", or (2) among the potential differences detected in the first bending-detection section and the second bending-detection section, a potential difference of which absolute value is smaller is considered as "GND", etc. In this case, even when the user bends the substrate in a slightly oblique direction, the image process can be performed in the same manner as when the user bends the substrate in a straight direction. This makes it possible to make the apparatus more user-friendly or easier to use. Alternatively, it is allowable that the potential difference detected by each of the first bending-detection section and the second bending-detection section is positively picked up so as to further detect an oblique bending (for example, bending in a direction of an axis located at a position between the bending axes C1 and C2) as well. For example, when the substrate is bend obliquely downwardly in the first embodiment, then the first bending-detection section detects "+" and the second bending-detection section detects "+" This can be set as an intentional operation by the user, so that a new image-process can be instructed to and executed by the apparatus.

What is claimed is:

1. A bending-detection apparatus which detects a bending of a device, comprising:
   a sheet-shaped substrate having flexibility;
   a detecting mechanism which detects a bending deformation of the substrate and which includes a sensor measuring an electric potential difference, and a plurality of detecting sections arranged on a surface of the substrate at a plurality of areas, respectively, each of the detecting sections having: a piezoelectric layer provided on a surface of the substrate; a plurality of first electrodes which are conducted with each other and each of which extends in an extending direction on a surface of the piezoelectric layer; and a plurality of second electrodes which are conducted with each other and each of which extends on the surface of the substrate in the extending direction, and which are arranged on the surface of the substrate alternately with the plurality of first electrodes,
   wherein the sensor measures an electric potential difference between a first electrode and a second electrode, among the plurality of first and second electrodes, of each of the detecting sections, to detect the bending deformation of the substrate based on the measured potential difference, and the extending direction in which the first and second electrodes extend is different among the plurality of detecting sections.

2. The bending-detection apparatus according to claim 1, wherein a thickness of the substrate is locally thinned in areas, of the substrate, at which at least one of the detecting sections is arranged respectively.

3. The bending-detection apparatus according to claim 1, wherein the first electrodes and the second electrodes are arranged on a surface, of the piezoelectric layer, not facing the substrate;
   the apparatus further includes an insulating layer provided on the surface of the piezoelectric layer; and the first electrodes and the second electrodes are sandwiched between the insulating layer and the piezoelectric layer.

4. The bending-detection apparatus according to claim 1, further comprising a display which has flexibility, which is provided integrally with the substrate, and which displays an image; and
a display control mechanism which controls the display to change an image displayed on the display, based on the bending deformation of the substrate detected in the detecting mechanism.

5. The bending-detection apparatus according to claim 4, wherein the piezoelectric layer is arranged on a surface, of the substrate, not facing the display of the substrate.

6. The bending-detection apparatus according to claim 1, wherein the substrate has a rectangular shape; and
the detecting mechanism includes two detecting sections arranged in a center line of a side among sides defining the substrate, and the first and the second electrodes in one of the two detecting sections extend parallel to the one side, and the first and the second electrodes in the other of the two detecting sections extend in a direction perpendicular to the one side.

7. The bending-detection apparatus according to claim 6, wherein the substrate has a rectangular shape; and
the detecting mechanism further includes another detecting section arranged at a corner of the substrate, and an angle defined by one side of the corner and an extending direction in which the first and the second electrodes extend in the another detecting section, and another angle defined by the other side of the corner and the extending direction are both approximately 45 degrees.

8. The bending-detection apparatus according to claim 1, wherein the substrate has a rectangular shape; and
the detecting mechanism includes four detecting sections each of which is arranged adjacent to a center of one of four sides defining the substrate, and an extending direction in which the first and the second electrodes extend in each of the detecting sections arranged adjacent to one of the four sides are approximately parallel to one of the four sides.

9. The bending-detection apparatus according to claim 1, wherein the second electrodes in each of the detecting sections are conducted with each other and are grounded.

10. The bending-detection apparatus according to claim 1, wherein an area, of the piezoelectric layer, sandwiched between the first and the second electrodes in each of the detecting sections is polarized parallel to a direction from the second electrodes toward the first electrodes.

* * * * *